United States Patent
Graycar et al.

(10) Patent No.: US 12,416,026 B2
(45) Date of Patent: Sep. 16, 2025

(54) EXPRESSION OF BETA-GLUCOSIDASE IN YEAST FOR IMPROVED ETHANOL PRODUCTION

(71) Applicant: DANISCO US INC., Palo Alto, CA (US)

(72) Inventors: Thomas P. Graycar, Pacifica, CA (US); Kerry Hollands, Newark, DE (US)

(73) Assignee: DANISCO US INC., Palo Alto, CA (US)

( * ) Notice: Subject to any disclaimer, the term of this patent is extended or adjusted under 35 U.S.C. 154(b) by 598 days.

(21) Appl. No.: 17/638,250

(22) PCT Filed: Aug. 20, 2020

(86) PCT No.: PCT/US2020/047150
§ 371 (c)(1),
(2) Date: Feb. 25, 2022

(87) PCT Pub. No.: WO2021/041141
PCT Pub. Date: Mar. 4, 2021

(65) Prior Publication Data
US 2022/0290189 A1    Sep. 15, 2022

Related U.S. Application Data

(60) Provisional application No. 62/893,374, filed on Aug. 29, 2019.

(51) Int. Cl.
*C12P 7/06* (2006.01)
*C12N 9/38* (2006.01)
*C12P 19/14* (2006.01)

(52) U.S. Cl.
CPC .............. *C12P 7/06* (2013.01); *C12N 9/2471* (2013.01); *C12P 19/14* (2013.01); *C12Y 302/01023* (2013.01)

(58) Field of Classification Search
None
See application file for complete search history.

(56) References Cited

U.S. PATENT DOCUMENTS

| | | | |
|---|---|---|---|
| 8,795,998 B2 | 8/2014 | Pronk et al. | |
| 8,956,851 B2 | 2/2015 | Argyros et al. | |
| 9,175,270 B2 | 11/2015 | Nevoigt et al. | |
| 9,181,566 B2 | 11/2015 | Dauner et al. | |
| 2010/0304438 A1 | 12/2010 | Scott et al. | |

FOREIGN PATENT DOCUMENTS

| | | |
|---|---|---|
| WO | 2008155665 A2 | 12/2008 |
| WO | 2012125951 A1 | 9/2012 |
| WO | 2013090053 A1 | 6/2013 |
| WO | 2015023989 A1 | 2/2015 |
| WO | 2015042064 A1 | 3/2015 |
| WO | 2015148272 A1 | 10/2015 |
| WO | 2016069541 A1 | 5/2016 |
| WO | 2018089333 A1 | 5/2018 |
| WO | 2018111792 A1 | 6/2018 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Accession E3QPM6. Jan. 11, 2011 (Year: 2011).*
Wei et al., "Simultaneous Utilization of Cellobiose, Xylose, and Acetic Acid from Lignocellulosic Biomass for Biofuel Production by an Engineered Yeast Platform", ACS Synthetic Biology, vol. 4, Issue 6, Jan. 14, 2015.
Altschul et al., "Basic Local Alignment Search Tool", J. Mol. Biol., 1990, vol. 215, pp. 403-410.
Altschul et al., "Local Alignment Statistics", Methods in Enzymology, 1996, vol. 266, pp. 460-480.
Devereux et al., "A comprehensive set of sequence analysis programs for the VAX", Nucleic Acids Research, 1984, vol. 12, No. 1, pp. 387-395.
Duskova et al., "Two glycerol uptake systems contribute to the high osmotolerance of Zygosaccharomyces rouxii", Molecular Microbiology, Aug. 2015, vol. 97, Issue 3, pp. 541-559.
Eauclaire et al., "Combinatorial metabolic pathway assembly in the yeast genome with RNA-guided Cas9", J. Ind. Microbiol. Biotechnol., 2016, vol. 43, pp. 1001-1015.
Feng et al., "Progressive Sequence Alignment as a Prerequisite to Correct Phylogenetic Trees", J. Mol. Evol., 1987, vol. 25, pp. 351-360.
Ferreira et al., "A Member of the Sugar Transporter Family, Stl1p Is the Glycerol/H+ Symporter in *Saccharomyces cerevisiae*", Molecular Biology of the Cell, Apr. 2005, vol. 16, pp. 2068-2076.
Gao et al., "Fast hemicellulose quantification via a simple one-step acid hydrolysis", Biotechnology and Bioengineering, Jun. 2014, vol. 111, Issue 6, pp. 1088-1096.
Gombert et al., "Improving conversion yield of fermentable sugars into fuel ethanol in 1st generation yeast-based production processes", Current Opinion in Biotechnology, 2015, vol. 33, pp. 81-86.
Henikoff et al., "Amino acid substitution matrices from protein blocks", Proc. Natl. Acad. Sci. USA, Nov. 1992, vol. 89, pp. 10915-10919.

(Continued)

*Primary Examiner* — Christian L Fronda

(57) ABSTRACT

Described are compositions and methods relating to the expression of β-glucosidase in yeast for use in industrial ethanol production. The yeast demonstrates increased ethanol production and reduced production of unwanted side-products, including acetate. Such yeast is particularly useful for large-scale ethanol production from starch substrates.

12 Claims, No Drawings
Specification includes a Sequence Listing.

(56) References Cited

OTHER PUBLICATIONS

Higgins et al., "Fast and sensitive multiple sequence alignments on a microcomputer", Cabios Communications, 1989, vol. 5, No. 2, pp. 151-153.

Karlin et al., "Applications and statistics for multiple high-scoring segments in molecular sequences", Proc. Natl. Acad. Sci. USA, Jun. 1993, vol. 90, pp. 5873-5877.

Needleman et al., "A General Method Applicable to the Search for Similarities in the Amino Acid Sequence of Two Proteins", J. Mol. Biol., 1970, vol. 48, pp. 443-453.

Pearson et al., "Improved tools for biological sequence comparison", Proc. Natl. Acad. Sci. USA, Apr. 1988, vol. 35, pp. 2444-2448.

Petersen et al., "SignalP 4.0: discriminating signal peptides from transmembrane regions", Nature Methods, 2011. vol. 8, pp. 785-786.

Sluiter et al., "Determination of Structural Carbohydrates and Lignin in Biomass: Laboratory Analytical Procedure", Technical Report NREL/TP-510-42618, National Renewable Energy Laboratory, Golden, CO, Apr. 2008, 18 pages.

Smith et al., "Comparison of Biosequences", Advances in Applied Mathematics, 1981, vol. 2, pp. 482-489.

Thompson et al., "Clustal W: improving the sensitivity of progressive multiple sequence alignment through sequence weighting, position-specific gap penalties and weight matrix choice", Nucleic Acids Research, 1994, vol. 22, No. 22, pp. 4673-4680.

Wei et al., "Simultaneous Utilization of Cellobiose, Xylose, and Acetic Acid from Lignocellulosic Biomass for Biofuel Production by an Engineered Yeast Platform", ACS Synthetic Biology, Jun. 19, 2015, vol. 4, No. 6, pp. 707-713.

Zhang et al., "Engineering of the glycerol decomposition pathway and cofactor regulation in an industrial yeast Improves ethanol production", J. Ind. Microbiol. Biotechnol., 2013, vol. 40, pp. 1153-1160.

International Search Report from PCT Application No. PCT/US2020/047150 dated Oct. 29, 2020, 5 pages.

* cited by examiner

EXPRESSION OF BETA-GLUCOSIDASE IN YEAST FOR IMPROVED ETHANOL PRODUCTION

TECHNICAL FIELD

The present compositions and methods relate to the expression of β-glucosidase in yeast for use in industrial ethanol production. The yeast demonstrates increased ethanol production and reduced production of unwanted side-products, including acetate. Such yeast is particularly useful for large-scale ethanol production from starch substrates.

REFERENCE TO SEQUENCE LISTING SUBMITTED ELECTRONICALLY

The official copy of the sequence listing is submitted electronically via EFS-Web as an ASCII formatted sequence listing with a file named "20190829_NB41307USPSP_SeqLst.txt created on Aug. 29, 2019 and having a size of 62 of kbs kilobytes and is filed concurrently with the specification. The sequence listing contained in this ASCII formatted document is part of the specification and is herein incorporated by reference in its entirety.

BACKGROUND

First-generation yeast-based ethanol production converts sugars into fuel ethanol. The annual fuel ethanol production by yeast is about 90 billion liters worldwide (Gombert, A. K. and van Maris, A. J. (2015) *Curr. Opin. Biotechnol.* 33:81-86). It is estimated that about 70% of the cost of ethanol production is the feedstock. Since the production volume is so large, even small yield improvements have massive economic impact across the industry.

The Renewable Fuel Standard (RFS) is a federal program that requires a minimum volume of renewable fuels to be blended into transportation fuel sold in the United States. The RFS originated with the Energy Policy Act of 2005 and was extended and expanded in the Energy Independence and Security Act of 2007. In 2010 the Environmental Protection Agency (EPA) established a process for companies to petition for new fuel pathways to qualify for the (RFS) program. A fuel pathway is a specific combination of (1) a feedstock, (2) a production process and (3) a fuel type, wherein each combination of three components represents a separate fuel pathway. Qualifying fuel pathways are assigned one or more D-codes corresponding to the type of Renewable Identification Number (RIN) they are eligible to generate. Conventional renewable fuel (e.g., from corn) is D6, advanced biofuel is D5, biodiesel is D4 and cellulosic biofuel is D3 or D7. Cellulosic Biofuel (D-Codes 3 and 7) must be produced from cellulose, hemicellulose or lignin.

RINs are tradable regulatory credits that represent a quantity of qualifying renewable fuel. RINs are assigned after a producer reports the production of a gallon of fuel to the EPA. Blenders demonstrate compliance with the RFS by turning RINs over to the EPA once the gallon of fuel is blended into transportation fuel. Because the RFS requires increasing amounts of advanced biofuels (including cellulosic biofuels) as time progresses, RINs have different values depending on the fuel pathway from which they are generated. For example, a D3 RIN is currently worth more than a D6 RIN.

The current National Renewable Energy Laboratory (NREL) laboratory analytical procedure (LAP) for determination of structural carbohydrates and lignin in biomass is described by Sluiter, A. et al. ((2008) NREL Laboratory Analytical Procedure NREL/TP-510-42618. Golden, CO: National Renewable Energy Laboratory). The method is based on two-step acid hydrolysis, in which biomass is first hydrolyzed using 72 wt % sulfuric acid at 30° C. for 1 h, followed by dilution to 4 wt % sulfuric acid for further hydrolysis at 121° C. for 1 h under autoclave conditions. A faster, single-step method has been described in which biomass is hydrolyzed in 4 wt % sulfuric acid for further hydrolysis at 121° C. for 1 h under autoclave conditions (Gao, X. et al. (2014) *Biotechnology and Bioengineering* 111:1088-96). In both methods, the products of hydrolysis are analyzed by HPLC. A limitation of these methods is that they cannot distinguish glucose derived from starch as opposed to glucose derived from cellulose and, therefore cannot be used to determine the fraction of glucose derived from cellulose in a mixed starch-cellulose feedstock. The EPA established corn kernel fiber as a qualified crop residue on Jul. 18, 2014.

As corn ethanol producers attempt to utilize corn fiber, as well as corn starch, to produce ethanol, there is a financial incentive to characterize as much ethanol as possible as D3 biofuel. However, the EPA requires accuracy in accounting and producers that have non-accurately characterized their biofuel can be subject to penalties. Accordingly, the need exists for an accurate method for determining the source of ethanol when mixed feedstocks of starch and cellulosic components are used to produce biofuels.

SUMMARY

The present compositions and methods relate to modified yeast that expresses β-glucosidase. Aspects and embodiments of the compositions and methods are described in the following, independently-numbered, paragraphs.

1. In one aspect, modified yeast cells derived from parental yeast cells are provided, the modified cells comprising a genetic alteration that causes the modified cells to produce an increased amount of β-glucosidase polypeptides compared to the parental cells, wherein the modified cells produce during fermentation more ethanol and/or less acetate compared to the amount of ethanol and acetate produced by otherwise identical parental yeast cells.

2. In some embodiments of the modified cells of paragraph 1, the genetic alteration comprises the introduction into the parental cells of a nucleic acid capable of directing the expression of a β-glucosidase polypeptide to a level above that of the parental cell grown under equivalent conditions.

3. In some embodiments of the modified cells of paragraph 1, the genetic alteration comprises the introduction of an expression cassette for expressing a β-glucosidase polypeptide.

4. In some embodiments of the modified cells of any of paragraphs 1-3, the cells further comprise an exogenous gene encoding a carbohydrate processing enzyme.

5. In some embodiments, the modified cells of any of paragraphs 1-4 further comprise a PKL pathway.

6. In some embodiments, the modified cells of any of paragraphs 1-5 further comprise an alteration in the glycerol pathway and/or the acetyl-CoA pathway.

7. In some embodiments, the modified cells of any of paragraphs 1-6 further comprise an alternative pathway for making ethanol.

8. In some embodiments of the modified cells of any of paragraphs 1-7, the modified cells further make reduced amounts of DP2 and/or DP3 compared to otherwise identical parental cells.

9. In some embodiments of the modified cells of any of paragraphs 1-8, the β-glucosidase polypeptides are derived from *Glomerella graminicola*.

10. In some embodiments of the modified cells of any of paragraphs 1-9, the β-glucosidase polypeptides have: (a) the amino acid sequence of SEQ ID NO: 1 or SEQ ID NO: 2, (b) an amino acid sequence having at least 80% amino acid sequence identity to SEQ ID NO: 1 or SEQ ID NO: 2, (c) the amino acid sequence of a mature polypeptide encoded by any of SEQ ID NOs: 11-16, (d) the amino acid sequence of a mature polypeptide encoded by a nucleic acid having at least 80% nucleic acid identity to any of SEQ ID NOs: 11-16, or (e) the amino acid sequence of a mature polypeptide encoded by a nucleic acid that hydridizes, under stringent condition, to any of SEQ ID NOs: 11-16, or the complement, thereof.

11. In some embodiments of the modified cells of any of paragraphs 1-10, the cells are of a *Saccharomyces* spp.

12. In another aspect, a method for increasing the production of alcohol and/or decreasing the production of acetate from yeast cells grown on a carbohydrate substrate is provided, comprising: introducing into parental yeast cells a genetic alteration that increases the production of β-glucosidase polypeptides compared to the amount produced in the parental cells.

13. In some embodiments of the method of paragraph 12, the cells having the introduced genetic alteration are the modified cells are the cells of any of paragraphs 1-11.

14. In some embodiments of the method of paragraph 12 or 13, the increased production of alcohol is at least 0.5%, at least 1.0%, at least 2.0% or at least 3.0%.

15. In some embodiments of the method of any of paragraphs 12-14, the decreased production of acetate is at least 1.0%, at least 2.0%, at least 4.0% or at least 6.0%.

16. In some embodiments of the method of any of paragraphs 12-15, the cells having the introduced genetic alteration comprise an exogenous PKL pathway.

These and other aspects and embodiments of present modified cells and methods will be apparent from the description, including any accompanying Drawings/Figures.

BRIEF DESCRIPTION OF THE SEQUENCES

SEQ ID NO: 1 represents the predicted mature amino acid sequence of ABG54.

SEQ ID NO: 2 represents the predicted mature amino acid sequence of FAB, which is the same as SEQ ID NO: 135 of WO2012125951 (Kaper et al.).

SEQ ID NO: 3 represents the predicted mature amino acid sequence of Mg3A.

SEQ ID NO: 4 represents the predicted mature amino acid sequence of TrBGL1.

SEQ ID NO: 5 represents the predicted native signal sequence for ABG54.

SEQ ID NO: 6 represents the predicted native signal sequence for FAB.

SEQ ID NO: 7 represents the predicted native signal sequence for Mg3A.

SEQ ID NO: 8 represents the predicted native signal sequence for TrBGL1.

SEQ ID NO: 9 represents the predicted MFalpha signal sequence.

SEQ ID NO: 10 represents the predicted SUC2 signal sequence.

SEQ ID NO: 11 represents the nucleotide sequence encoding native-ABG54 in pYKH1127, GKH-0464, G3020, G3014, GKH-0737 and GKH-0732.

SEQ ID NO: 12 represents the nucleotide sequence encoding MFalpha-ABG54 in pYKH1139 and GKH-0459.

SEQ ID NO: 13 represents the nucleotide sequence encoding SUC2-ABG54 in GKH-0484.

SEQ ID NO: 14 represents the nucleotide sequence encoding native-FAB in pYKH1135 and GKH-0455.

SEQ ID NO: 15 represents the nucleotide sequence encoding MFalpha-FAB in pYKH1095 and GKH-0450.

SEQ ID NO: 16 represents the nucleotide sequence encoding SUC2-FAB in GKH-0466.

SEQ ID NO: 17 represents the nucleotide sequence encoding native-Mg3A in pYKH1097.

SEQ ID NO: 18 represents the nucleotide sequence encoding MFalpha-Mg3A in pYKH1096.

SEQ ID NO: 19 represents the nucleotide sequence encoding native-TrBGL1 in pYKH1099.

SEQ ID NO: 20 represents the nucleotide sequence encoding MFalpha-TrBGL1 in pYKH1098.

DETAILED DESCRIPTION

I. Definitions

Prior to describing the present yeast and methods in detail, the following terms are defined for clarity. Terms not defined should be accorded their ordinary meanings as used in the relevant art.

As used herein, the term "alcohol" refers to an organic compound in which a hydroxyl functional group (—OH) is bound to a saturated carbon atom.

As used herein, the terms "yeast cells," "yeast strains," or simply "yeast" refer to organisms from the phyla Ascomycota and Basidiomycota. Exemplary yeast is budding yeast from the order Saccharomycetales. Particular examples of yeast are *Saccharomyces* spp., including but not limited to *S. cerevisiae*. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "engineered yeast cells," "variant yeast cells," "modified yeast cells," or similar phrases, refer to yeast that include genetic modifications and characteristics described herein. Variant/modified yeast do not include naturally occurring yeast.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins," or "homologs." Such proteins can be derived from organisms of different genera and/or species, or different classes of organisms (e.g., bacteria and fungi), or artificially designed. Related proteins also encompass homologs determined by primary sequence analysis, determined by secondary or tertiary structure analysis, or determined by immunological cross-reactivity, or determined by their functions.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.,* 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, WI); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et a. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'5, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) *Nucleic Acids Res.* 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF |

Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M Na3 citrate, pH 7.0). Hybridized, duplex nucleic acids are characterized by a melting temperature ($T_m$), where one-half of the hybridized nucleic acids are unpaired with the complementary strand. Mismatched nucleotides within the duplex lower the $T_m$. A nucleic acid encoding a variant α-amylase may have a $T_m$ reduced by 1° C.-3° C. or more compared to a duplex formed between the nucleotide of SEQ ID NO: 2 and its identical complement.

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype. The term "allele" is generally preferred when an organism contains more than one similar genes, in which case each different similar gene is referred to as a distinct "allele."

As used herein, the term "expressing a polypeptide" and similar terms refers to the cellular process of producing a polypeptide using the translation machinery (e.g., ribosomes) of the cell.

As used herein, an "expression cassette" refers to a DNA fragment that includes a promoter, and amino acid coding region and a terminator (i.e., promoter::amino acid coding region::terminator) and other nucleic acid sequence needed to allow the encoded polypeptide to be produced in a cell. Expression cassettes can be exogenous (i.e., introduced into a cell) or endogenous (i.e., extant in a cell).

As used herein, the terms "wild-type" and "native" are used interchangeably and refer to genes, proteins or strains found in nature, or that are not intentionally modified for the advantage of the presently described yeast.

As used herein, the term "protein of interest" refers to a polypeptide that is desired to be expressed in modified yeast. Such a protein can be an enzyme, a substrate-binding protein, a surface-active protein, a structural protein, a selectable marker, a signal transducer, a receptor, a transporter, a transcription factor, a translation factor, a co-factor, or the like, and can be expressed. The protein of interest is encoded by an endogenous gene or a heterologous gene (i.e., gene of interest) relative to the parental strain. The protein of interest can be expressed intracellularly or as a secreted protein.

As used herein, the terms "genetic manipulation" and "genetic alteration" are used interchangeably and refer to the alteration/change of a nucleic acid sequence. The alteration can include but is not limited to a substitution, deletion, insertion or chemical modification of at least one nucleic acid in the nucleic acid sequence.

As used herein, a "functional polypeptide/protein" is a protein that possesses an activity, such as an enzymatic activity, a binding activity, a surface-active property, a signal transducer, a receptor, a transporter, a transcription factor, a translation factor, a co-factor, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, yeast cells have been "modified to prevent the production of a specified protein" if they have been genetically or chemically altered to prevent the production of a functional protein/polypeptide that exhibits an activity characteristic of the wild-type protein. Such modifications include, but are not limited to, deletion or disruption of the gene encoding the protein (as described, herein), modification of the gene such that the encoded polypeptide lacks the aforementioned activity, modification of the gene to affect post-translational processing or stability, and combinations, thereof.

As used herein. "aerobic fermentation" refers to growth in the presence of oxygen.

As used herein, "anaerobic fermentation" refers to growth in the absence of oxygen.

As used herein, the expression "end of fermentation" refers to the stage of fermentation when the economic advantage of continuing fermentation to produce a small amount of additional alcohol is exceeded by the cost of continuing fermentation in terms of fixed and variable costs. In a more general sense, "end of fermentation" refers to the point where a fermentation will no longer produce a significant amount of additional alcohol, i.e., no more than about 1% additional alcohol, or no more substrate left for further alcohol production.

As used herein, the phrase "degree of polymerization" (DP) refers to the number of anhydroglucopyranose units in a given saccharide. An examples of DP1 is the monosaccharides glucose. Examples of DP2 are the disaccharides maltose and isomaltose.

As used herein, the expression "carbon flux" refers to the rate of turnover of carbon molecules through a metabolic pathway. Carbon flux is regulated by enzymes involved in metabolic pathways, such as the pathway for glucose metabolism and the pathway for maltose metabolism.

As used herein, the singular articles "a," "an" and "the" encompass the plural referents unless the context clearly dictates otherwise. All references cited herein are hereby incorporated by reference in their entirety. The following abbreviations/acronyms have the following meanings unless otherwise specified:

° C. degrees Centigrade
AA α-amylase
AADH acetaldehyde dehydrogenases
ADH alcohol dehydrogenase
bp base pairs
DNA deoxyribonucleic acid
ds or DS dry solids
DP degree of polymerization
EC enzyme commission
EtOH ethanol
g or gm gram
g/L grams per liter
GA glucoamylase
HPLC high performance liquid chromatography
hr or h hour
M molar
mg milligram
min minute
mL or ml milliliter
mM millimolar
N normal
n/a not applicable
n/d no data
nm nanometer
PCR polymerase chain reaction
PKL phosphoketolase
ppm parts per million
PTA phosphotransacetylase
RPM revolutions per minute
Δ relating to a deletion
μg microgram
μL and μl microliter
μM micromolar II. Modified Yeast Cells Expressing β-Glucosidase Described are modified yeast cells that express β-glucosidase, and methods of use, thereof. The yeast produces increased amounts of ethanol, decreased amounts of acetate, and offer additional advantages compared to conventional yeast. The additional ethanol results from the utilization of non-starch-derived β-D-linked glucan substrates, for example, cellobiose and other cellooligosaccharide substrates, and may qualify for D3 RIN credits. Expression of β-glucosidase in yeast was inspired by the observation that contacting stillage with a cocktail of eight glycosyl hydrolase enzymes and enriched for β-glucosidase, liberated more glucose compared to cocktails enriched for a different glycosyl hydrolase.

Yeast can be selective in their ability to express exogenous proteins, and expression of β-glucosidase is no exception. Expression of β-glucosidase in yeast was not straightforward and suitable yeast were not readily obtained. It is also surprising that the expression of β-glucosidase by an ethanologen, so far downstream of initial starch liquefaction, would lead to the observed benefits in ethanol and acetate production. Expression of β-glucosidase was also found to benefit ethanol and acetate production in combination with an exogenous PKL pathway and in combination with glucoamylase expression.

In some embodiments, the increase in ethanol production by the modified cells is an increase of at least 0.5%, at least 0.7%, at least 0.9%, at least 1.2%, at least 1.5%, at least 2.0%, at least 3.0%, or more, compared to the amount of ethanol produced by parental cells grown under the same conditions.

In some embodiments, the decrease in acetate production by the modified cells is an decrease of at least 0.5%, at least 1.0%, at least 2.0%, at least 3.0%, at least 4.0%, at least 5.0%, at least 6.0%, or more, compared to the amount of acetate produced by parental cells grown under the same conditions.

Preferably, increased β-glucosidase expression is achieved by genetic manipulation using sequence-specific molecular biology techniques, as opposed to chemical mutagenesis, which is generally not targeted to specific nucleic acid sequences. However, chemical mutagenesis is not excluded as a method for making modified yeast cells.

In some embodiments, the present compositions and methods involve introducing into yeast cells a nucleic acid capable of directing the expression, or over-expression, of a β-glucosidase polypeptide. Particular methods include but are not limited to (i) introducing an exogenous expression cassette for producing the polypeptide into a host cell, optionally in addition to an endogenous expression cassette, (ii) substituting an exogenous expression cassette with an endogenous cassette that allows the production of an increased amount of the polypeptide, (iii) modifying the promoter of an endogenous expression cassette to increase expression, (iv) increase copy number of the same or different cassettes for over-expression of β-glucosidase, and/or (v) modifying any aspect of the host cell to increase the half-life of the polypeptide in the host cell.

In some embodiments, the parental cell that is modified already includes a gene of interest, such as a gene encoding a selectable marker, carbohydrate-processing enzyme, or other polypeptide. In some embodiments, a gene of interest is subsequently introduced into the modified cells.

In some embodiments, the parental cell that is modified already includes an engineered pathway of interest, such as a PKL pathway to increase ethanol production, or any other pathway to increase alcohol production.

In some embodiments of the present compositions and methods, the amino acid sequence of the β-glucosidase polypeptide that is expressed in modified yeast cells has at least about 80%, at least about 85%, at least about 87%, at least about 90%, at least about 91%, at least about 92%, at least about 93%, at least about 94%, at least about 95%, at least about 96%, at least about 97%, at least about 98%, or even at least about 99% identity, to SEQ ID NO: 1 or SEQ ID NO: 2.

In some embodiments of the present compositions and methods, β-glucosidase polypeptide has an the amino acid sequence of a mature polypeptide encoded by a nucleic acid having at least about 80%, at least about 85%, at least about 87%, at least about 90%, at least about 91%, at least about 92%, at least about 93%, at least about 94%, at least about 95%, at least about 96%, at least about 97%, at least about 98%, or even at least about 99% identity nucleic acid identity to any of SEQ ID NOs: 11-16, or the amino acid sequence of a mature polypeptide encoded by a nucleic acid that hybridizes, under stringent condition, to any of SEQ ID NOs: 11-16, or the complement, thereof.

III. Modified Yeast Cells Having Increased β-Glucosidase Expression in Combination with Genes of an Exogenous PKL Pathway Increased expression of β-glucosidase can be combined with expression of genes in the PKL pathway to further increase ethanol production. Engineered yeast cells having a heterologous PKL pathway have been previously described in WO2015148272 (Miasnikov et al.). These cells express heterologous phosphoketolase (PKL), phosphotransacetylase (PTA) and acetylating acetyl dehydrogenase (AADH), optionally with other enzymes, to channel carbon flux away from the glycerol pathway and toward the synthesis of acetyl-CoA, which is then converted to ethanol. Such modified cells are capable of increased ethanol production in a fermentation process when compared to otherwise-identical parent yeast cells.

IV. Combination of Increased β-Glucosidase Production with Other Mutations that Affect Alcohol Production In some embodiments, in addition to expressing increased amounts of β-glucosidase polypeptides, optionally in combination with introducing an exogenous PKL pathway, the present modified yeast cells include additional beneficial modifications.

The modified cells may further include mutations that result in attenuation of the native glycerol biosynthesis pathway and/or reuse glycerol pathway, which are known to increase alcohol production. Methods for attenuation of the glycerol biosynthesis pathway in yeast are known and include reduction or elimination of endogenous NAD-dependent glycerol 3-phosphate dehydrogenase (GPD) or glycerol phosphate phosphatase activity (GPP), for example by disruption of one or more of the genes GPD1, GPD2, GPP1 and/or GPP2. See, e.g., U.S. Pat. No. 9,175,270 (Elke et al.), U.S. Pat. No. 8,795,998 (Pronk et al.) and U.S. Pat. No. 8,956,851 (Argyros et al.). Methods to enhance the reuse glycerol pathway by over expression of glycerol dehydrogenase (GCY1) and dihydroxyacetone kinase (DAK1) to convert glycerol to dihydroxyacetone phosphate (Zhang et al. (2013) *J. Ind. Microbiol. Biotechnol.* 40:1153-60).

The modified yeast may further feature increased acetyl-CoA synthase (also referred to acetyl-CoA ligase) activity (EC 6.2.1.1) to scavenge (i.e., capture) acetate produced by chemical or enzymatic hydrolysis of acetyl-phosphate (or present in the culture medium of the yeast for any other reason) and converts it to Ac-CoA. This partially reduces the undesirable effect of acetate on the growth of yeast cells and may further contribute to an improvement in alcohol yield. Increasing acetyl-CoA synthase activity may be accomplished by introducing a heterologous acetyl-CoA synthase gene into cells, increasing the expression of an endogenous acetyl-CoA synthase gene and the like.

In some embodiments the modified cells may further include a heterologous gene encoding a protein with $NAD^+$-dependent acetylating acetaldehyde dehydrogenase activity and/or a heterologous gene encoding a pyruvate-formate lyase. The introduction of such genes in combination with attenuation of the glycerol pathway is described. e.g., in U.S. Pat. No. 8,795,998 (Pronk et al.). In some embodiments of the present compositions and methods the yeast expressly lacks a heterologous gene(s) encoding an acetylating acetaldehyde dehydrogenase, a pyruvate-formate lyase or both.

In some embodiments, the present modified yeast cells may further over-express a sugar transporter-like (STL) polypeptide to increase the uptake of glycerol (see, e.g., Ferreira et al. (2005) *Mol. Biol. Cell.* 16:2068-76; Dušková et al. (2015) *Mol. Microbiol.* 97:541-59 and WO 2015023989 A1) to increase ethanol production and reduce acetate.

In some embodiments, the present modified yeast cells further include a butanol biosynthetic pathway. In some embodiments, the butanol biosynthetic pathway is an isobutanol biosynthetic pathway. In some embodiments, the isobutanol biosynthetic pathway comprises a polynucleotide encoding a polypeptide that catalyzes a substrate to product conversion selected from the group consisting of: (a) pyruvate to acetolactate; (b) acetolactate to 2,3-dihydroxyisovalerate; (c) 2,3-dihydroxyisovalerate to 2-ketoisovalerate; (d) 2-ketoisovalerate to isobutyraldehyde; and (e) isobutyraldehyde to isobutanol. In some embodiments, the isobutanol biosynthetic pathway comprises polynucleotides encoding polypeptides having acetolactate synthase, keto acid reductoisomerase, dihydroxy acid dehydratase, ketoisovalerate decarboxylase, and alcohol dehydrogenase activity.

In some embodiments, the modified yeast cells comprising a butanol biosynthetic pathway further comprise a modification in a polynucleotide encoding a polypeptide having pyruvate decarboxylase activity. In some embodiments, the yeast cells comprise a deletion, mutation, and/or substitution in an endogenous polynucleotide encoding a polypeptide having pyruvate decarboxylase activity. In some embodiments, the polypeptide having pyruvate decarboxylase activity is selected from the group consisting of: PDC1, PDC5, PDC6, and combinations thereof. In some embodiments, the yeast cells further comprise a deletion, mutation, and/or substitution in one or more endogenous polynucleotides encoding FRA2, ALD6, ADH1, GPD2, BDH1, DLS1, DPB3, CPR1, MAL23C, MNN4, PAB1, TMN2, HAC1, PTC1, PTC2, OSM1, GIS1, CRZ1, HUG1, GDS1, CYB2P, SFC1, MVB12, LDB10, C5SD, GIC1, GIC2 and/or YMR226C.

V. Combination of Increased Expression β-Glucosidase with Other Beneficial Mutations In some embodiments, in addition to increased expression of β-glucosidase polypeptides, optionally in combination with other genetic modifications that benefit alcohol production and/or acetate reduction, the present modified yeast cells further include any number of additional genes of interest encoding proteins of interest. Additional genes of interest may be introduced before, during, or after genetic manipulations that result in the increased production of β-glucosidase polypeptides. Proteins of interest, include selectable markers, carbohydrate-processing enzymes, and other commercially-relevant polypeptides, including but not limited to an enzyme selected from the group consisting of a dehydrogenase, a transketolase, a phosphoketolase, a transaldolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. Proteins of interest may be secreted, glycosylated, and otherwise-modified.

VI. Use of the Modified Yeast for Increased Alcohol Production

The present compositions and methods include methods for increasing alcohol production and/or reducing glycerol production, in fermentation reactions. Such methods are not limited to a particular fermentation process. The present engineered yeast is expected to be a "drop-in" replacement for convention yeast in any alcohol fermentation facility. While primarily intended for fuel alcohol production, the present yeast can also be used for the production of potable alcohol, including wine and beer.

VII. Yeast Cells Suitable for Modification

Yeasts are unicellular eukaryotic microorganisms classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces, Lachancea* and *Schizosaccharomyces* spp. Numerous yeast strains are commercially available, many of which have been selected or genetically engineered for desired characteristics, such as high alcohol production, rapid growth rate, and the like. Some yeasts have been genetically engineered to produce heterologous enzymes, such as glucoamylase or α-amylase.

VII. Substrates and Products

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Alcohol fermentation products include organic compound having a hydroxyl functional group (—OH) is bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol.

These and other aspects and embodiments of the present yeast strains and methods will be apparent to the skilled person in view of the present description. The following examples are intended to further illustrate, but not limit, the compositions and methods.

EXAMPLES

Example 1: Addition of β-Glucosidases to Stillage

Fermentation broth from submerged fermentation cultures expressing eight different glycosyl hydrolase enzymes, including ABG54 β-glucosidase, was prepared for analysis by filtration to remove cell mass using 96-well Millipore filter plates. Filtration was followed by exchange of each enzyme from culture broth into 20 mM sodium acetate buffer, pH 5.0, 0.005% TWEEN®-80, using 96-well ZEBA™ Spin desalting plates (ThermoFisher, Cat. No.: 89807).

An Agilent HPLC 1290 INFINITY™ system was used to quantify the protein obtained from each culture using a Waters ACQUITY UPLC® C4BEH 300 column (1.7 μm, 1×50 mm). A six-minute program was used starting with an initial gradient from 5% to 33% acetonitrile (Sigma-Aldrich) in 0.5 minutes, followed by a gradient from 33% to 48% acetonitrile in 4.5 minutes, and then a step gradient to 90% acetonitrile. A protein standard curve based on purified *Trichoderma reesei* Bgl1 (referred to as TrBGL1, below) was used to quantify the enzyme sample preparations. Prior to running enzyme samples on the HPLC system all the proteins were first deglycosylated using endoglycosidase-H.

Whole stillage sampled from a grain ethanol production plant was centrifuged and the resulting supernatant passed through a 0.2 µm membrane filter. A 20% volume of 100 mM sodium acetate buffer, pH 5.0, with 0.005% Tween 80 was added to the whole stillage substrate for enzyme activity assays. Glycosyl hydrolase enzymes were added to the filtered whole stillage supernatant to identify enzymes capable of releasing glucose from the soluble recalcitrant oligosaccharides.

Glycosyl hydrolase reactions with the soluble recalcitrant oligosaccharide substrate were performed in 96-well microtiter plates containing 150 µl of the buffered whole stillage supernatant, a 3 µg protein blend of all eight glycosyl hydrolases, and 6 µg of each individual glycosyl hydrolase combined with the protein blend. Reaction plates were sealed, and incubated at 32° C. for 18 hours with 250 RPM mixing. Immediately following the incubation, the plates were unsealed and 150 µl of 0.1 N sulfuric acid was mixed into the well contents to quench the hydrolysis reactions. The amount of glucose product generated by the enzymatic hydrolysis of recalcitrant oligosaccharides was measured using an ABTS assay for glucose.

An ABTS stock solution containing 2,2'-azino-bis(3-ethylbenzothiazoline-6-sulfonic acid) di-ammonium salt (Sigma Aldrich) at 2.88 mg/ml, horseradish peroxidase (Sigma Aldrich) at 0.11 U/m and glucose oxidase (OXYGO™ HP 5000L. DuPont) at 1.05 U/ml was prepared in 50 mM sodium phosphate buffer, pH 7. 95 µl of the ABTS stock solution was transferred into the wells of a 96-well microtiter plate, 5 µl of the quenched reaction plates was pipetted into the assay plates containing the ABTS solution. Assay plates were loaded into a microtiter plate reader set for a 3-min kinetic measurement at an absorbance setting of 405 m with a 9-sec read interval and a 60-second lag. A 5-sec shaking step was used prior to the kinetic measurement for mixing and to eliminate any air bubbles in the assay plate wells. The amount of glucose produced for each sample reaction was calculated using a standard curve generated with glucose standards and the same ABTS assay. The results are shown in Table 1. The enzyme composition enriched for Enzyme H (the β-glucosidase ABG54) produced the most glucose from a stillage substrate.

TABLE 1

Production of glucose from recalcitrant soluble oligosaccharides in whole stillage

| Enzyme | Glucose produced (mM) |
| --- | --- |
| Protein blend (PB) | 7.99 |
| PB + Enzyme A | 8.37 |
| PB + Enzyme B | 8.16 |
| PB + Enzyme C | 8.17 |
| PB + Enzyme D | 8.15 |
| PB + Enzyme E | 8.22 |
| PB + Enzyme F | 8.08 |
| PB + Enzyme G | 8.10 |
| PB + Enzyme H | 9.65 |

Example 2: Materials and Methods for Examples 2-8

Liquefact Preparation

Liquefact (Ground corn slurry) was prepared by adding 600 ppm of urea, 0.124 SAPU/g ds FERMGEN™ 2.5×(acid fungal protease), 0.33 GAU/g ds variant *Trichoderma* glucoamylase (TrGA) and 1.46 SSCU/g ds *Aspergillus* α-amylase (AkAA), adjusted to a pH of 4.8. For evaluation of strains expressing glucoamylase, the dose of glucoamylase was reduced to 0.1 GAU/g ds. In certain experiments, 5 g/L cellobiose was also added to the liquefact.

Serum Vial Assays 2 mL of YPD in 24-well plates were inoculated with yeast cells and the cells allowed to grow overnight, 5 ml prepared liquefact was aliquoted to serum vials (Chemglass, Catalog No.: CG-4904-01) and yeast was added to each vial for a final OD of about 0.2-0.4. The lids of the vials were screw on and punctured with a needle (BD, Catalog No.: 305111) for ventilation (to release $CO_2$), then incubated at 32° C. with shaking (200 RPM) for 55 hours.

Shake Flask Assays

100 µL of concentrated yeast overnight culture was added to each of a number of shake flasks filled with 50 g prepared liquefact for a final OD of 0.3. The flasks were incubated at 32° C. with shaking (200 RPM) for 55 hours.

HPLC Analysis

Samples from serum vial and shake flask experiments were filtered through 0.2 µM PTFE filters and the filtrates analyzed for acetate, ethanol, glycerol, glucose, DP2, DP3 and DP4+ content by HPLC (Waters e2695 series) using Bio-Rad Aminex HPX-87H columns at 65° C., with an isocratic flow rate of 0.6 ml/min in 0.01 N $H_2SO_4$ eluent. A 2.5 µl sample injection volume was used. Calibration standards were used for quantification of acetate, ethanol, glycerol and glucose. Values are expressed in g/L.

Growth of Strains for β-Glucosidase Activity Determination

Yeast strains were inoculated into 2 ml synthetic complete medium lacking uracil (SC-ura) or YPD medium in 24-well plates and the cells allowed to grow overnight. Cultures were filtered through a 0.2 µm filter plate (PALL AcroPrep Advance, GHP membrane) and the resulting filtrates assayed for β-glucosidase activity.

β-Glucosidase Activity Assay

A 4-nitrophenyl-β-D-glucopyranoside (pNPG) substrate solution was prepared by dissolving 0.006 g pNPG in 20 ml 0.05 M sodium acetate buffer (0.05 M sodium acetate, 0.1% (v/v) Polyethylene glycerol 8000, pH 4.8). 100 µl pNPG substrate solution was mixed with 20 µl filtered culture supernatant or β-glucosidase standard and incubated for 45 min at 30'C. The reaction was stopped by adding 50 µl 1 M sodium carbonate and incubating for 1 min at room temperature, then absorbance at 405 m was measured. β-glucosidase activity in culture supernatants was calculated by comparison to a standard curve generated using serially diluted β-glucosidase standard.

Signal Sequence Prediction

The determination of signal sequence cleavage sites was predicted using SignalP version 4.1 (Petersen, T. N. et al. (2011) Nature Methods, 8:785-86) with default parameters. It will be understood that actual signal sequence cleavage sites, and therefore the N-termini of mature secreted polypeptides, may differ by a few amino acid residues or may vary within a population of secreted polypeptides.

Example 3: Screening for Expression of β-Glucosidases in *S. cerevisiae*

Genes coding for four different β-glucosidases (SEQ ID NOs: 1-4), codon optimized for *Saccharomyces cerevisiae*, were cloned between the SpeI and NotI restriction sites in pJT257 (described in U.S. Pat. No. 9,181,566). In the resulting plasmids, expression of the β-glucosidase is under control of the FBA1 promoter and FBA1 terminator from *S. cerevisiae* (see, e.g., WO2018/111792). A second set of plasmids was constructed containing genes coding for the same four β-glucosidases but with the native signal sequence (SEQ ID NOs: 5-8) removed and replaced with the signal sequence from the *S. cerevisiae* mating factor α (MFalpha; SEQ ID NO: 9). Plasmids were designated as show in Table 2. Note that FAB is hybrid enzyme derived from portions of the β-glucosidases from *Fusarium vesticilloies, Rasamsonia emersonii* and *Hypocrea* (*Trichoderma*) *jecorina*, which is described in WO2012125951 (Kaper et al.) as SEQ ID NO: 135.

TABLE 2

β-glucosidase expression plasmids

| Plasmid name | β-glucosidase | SEQ ID NO | Signal sequence | SEQ ID NO | Source organism |
|---|---|---|---|---|---|
| pYKH1127 | ABG54 | 1 | native | 5 | *Gomerella graninicola* |
| pYKH1139 | | | MFalpha | 9 | |
| pYKH1135 | FAB | 2 | native | 6 | *Fusarium vesticilloies/* |
| pYKH1095 | | | MFalpha | 9 | *Rasamsonia emersonii/ Hypocrea jecorina* |
| pYKH1097 | Mg3A | 3 | native | 7 | *Magnaporthe grisea* |
| pYKH1096 | | | MFalpha | 9 | |
| pYKH1099 | TrBGL1 | 4 | native | 8 | *Hypocrea jecorina* |
| pYKH1098 | | | MFalpha | 9 | |

The plasmids listed in Table 2 were transformed into strain FG-ura3 and transformants were selected by growth on synthetic complete medium lacking uracil (SC-ura). FG-ura3 is a derivative of FERMAX™ Gold (hereafter abbreviated, "FG") in which the ura3 gene has been deleted. The construction of FG-ara3 is described in WO2018111792A1. FG-ura3 was also transformed with the control plasmid pPOL00040 that lacks a β-glucosidase coding sequence. Transformants were grown overnight in SC-ura liquid medium, and β-glucosidase activity in the culture medium was measured as described in Example 2. The results from two such experiments are shown in Table 3.

TABLE 3

β-glucosidase activity measured in FG-ura3 transformed with β-glucosidase expression plasmids

| Plasmid | Enzyme | Signal sequence | $A_{405}$ (Exp. 1) | $A_{405}$ (Exp. 2) |
|---|---|---|---|---|
| pYKH1127 | ABG54 | native | 0.107 ± 0.018 | 0.174 ± 0.023 |
| pYKH1139 | | MFalpha | n/d | 0.244 ± 0.055 |
| pYKH1135 | FAB | native | 0.086 ± 0.004 | 0.156 ± 0.009 |
| pYKH1095 | | MFalpha | 0.152 ± 0.014 | 0.308 ± 0.057 |
| pYKH1097 | Mg3A | native | 0.005 ± 0.001 | n/d |
| pYKH1096 | | MFalpha | 0.004 ± 0.001 | n/d |
| pYKH1099 | TrBGL1 | native | 0.004 ± 0.001 | n/d |
| pYKH1098 | | MFalpha | 0.004 ± 0.000 | n/d |
| pPOL00040 | none | n/a | 0.003 ± 0.001 | 0.003 ± 0.001 |

$A_{405}$ was higher for strains containing plasmids encoding ABG54 or FAB than for the control strain transformed with pPOL00040. This demonstrates that strains encoding ABG54 or FAB express β-glucosidase activity. β-glucosidase activity was detected for strains expressing ABG54 or FAB with either their native signal sequences or the MFalpha signal sequence. In contrast, strains containing plasmids encoding Mg3A or TrBGL1 did not appear to produce β-glucosidase activity above that measured for the negative control strain transformed with pPOL00040.

Example 4: Strains with Integrated Expression Cassettes for ABG54 or FAB

Expression cassettes coding for ABG54 with its native signal sequence, ABG54 with the MFalpha signal sequence, FAB with its native signal sequence (SEQ ID NO:6) or FAB with the MFalpha signal sequence (SEQ ID NO:9) were amplified by PCR from plasmids pYKH1127, pYKH1139, pYKH1135 or pYKH1095, respectively, using primers that incorporate regions of homology to a target site at the PAM1 locus in *S. cerevisiae*. Each of the amplified DNA fragments was used as a donor DNA for CRISPR-mediated integration at the PAM1 locus in FG. Integration of the β-glucosidase expression cassettes was confirmed by colony PCR, and the resulting strains were designated as shown in Table 4.

Strains were also constructed in which the native signal sequence of ABG54 or FAB was replaced with the signal sequence from the *S. cerevisiae* invertase gene, SUC2 (SEQ ID NO: 10). These strains were constructed by transforming FG with two overlapping DNA fragments—one containing the *S. cerevisiae* FBA1 promoter joined to the SUC2 signal sequence, and the other containing the ABG54 or FAB coding sequence (without the native signal sequence) joined to the FBA1 terminator. These fragments were assembled and integrated at the PAM1 locus using the procedure described in EauClaire et. al. (2016) *J. Ind. Microbiol. Biotechnol.* 43:1001-15. Correct assembly and integration of the β-glucosidase expression cassettes was confirmed by colony PCR. The resulting strains were designated as shown in Table 4.

Four clones of each strain, together with the parental strain FG, were grown overnight in YPD liquid medium, and β-glucosidase activity in the resulting culture medium was measured as described in Example 2. The results are shown in Table 4.

TABLE 4

β-glucosidase activity secreted by strains encoding ABG54 or FAB, versus FG.

| Strain | β-glucosidase expressed | Signal sequence | $A_{405}$ |
|---|---|---|---|
| GKH-0464 | ABG54 | native | 0.970 ± 0.031 |
| GKH-0459 | | MFalpha | 1.240 ± 0.107 |
| GKH-0484 | | SUC2 | 0.922 ± 0.016 |
| GKH-0455 | FAB | native | 0.248 ± 0.011 |
| GKH-0450 | | MFalpha | 0.666 ± 0.039 |
| GKH-0466 | | SUC2 | 0.170 ± 0.053 |
| FG | n/a | n/a | 0.088 ± 0.012 |

A$_{405}$ was higher for the new strains with integrated β-glucosidase expression cassettes than for the parental FG strain. This indicates that strains GKH-0464, GKH-0459, GKH-0484, GKH-0455, GKH-0450 and GKH-0466 all express β-glucosidase activity.

Example 5. Ethanol Production by *S. cerevisiae* Strains Expressing β-Glucosidase in Vial Assays Four clones of each strain listed in Table 4 were screened for ethanol production, relative to the parent strain FG. Strains were growth in corn liquefact in serum vials, and ethanol production was analyzed after 55 h fermentation as described in Example 2. The results are shown in Table 5.

TABLE 5

Performance of β-glucosidase expressing yeast strains versus FG in vial assays

| Strain | β-glucosidase | Signal sequence | Ethanol (g/L) | Ethanol increase vs FG (%) |
|---|---|---|---|---|
| GKH-0464 | ABG54 | native | 142.41 ± 0.31 | 1.5 |
| GKH-0459 | | MFalpha | 141.35 ± 0.59 | 0.7 |
| GKH-0484 | | SUC2 | 142.02 ± 0.92 | 1.2 |
| GKH-0455 | FAB | native | 141.99 ± 0.12 | 1.2 |
| GKH-0450 | | MFalpha | 138.94 ± 0.41 | −1.0 |
| GKH-0466 | | SUC2 | 142.31 ± 0.33 | 1.4 |
| FG | n/a | n/a | 140.37 ± 0.40 | n/a |

The β-glucosidase expressing strains GKH-0464, GKH-0459, GKH-0484, GKH-0455 and GKH-0466 resulted in up to 1.5% increased ethanol production compared to the parental FG strain.

Example 6: Ethanol Production by *S. cerevisiae* Strains Expressing β-Glucosidase in Shake Flask Assays To further examine the benefits of β-glucosidase expression, the performance of strains GKH-0464 and GKH-0484 were analyzed more precisely using a shake flask assay. Strains GKH-0464, GKH-0484 or the parental strain FG were grown for 55 h in corn liquefact, and their fermentation products analyzed as described in Example 2. In a second set of flasks, approx. 5 g/L cellobiose was added prior to inoculation with the yeast. The results are shown in Table 6.

The β-glucosidase-expressing strains GKH-0464 and GKH-0484 resulted in up to 3.3% increased ethanol production compared to the parental FG strain. GKH-0464 and GKH-0484 also resulted in up to 6.3% decreased acetate, as well as decreased DP2 and decreased DP3 compared to the parental strain. For fermentations with FG, addition of approximately 5 g/L cellobiose to the liquefact prior to inoculation with the yeast resulted in a corresponding increase in DP2 at the end of fermentation. This indicates that the added cellobiose was not consumed during fermentation with FG. In contrast, for GKH-0464 and GKH-0484, the DP2 concentration at the end of fermentation was similar for liquefact with or without added cellobiose. This indicates that cellobiose can be consumed during fermentation with GKH-0464 and GKH-0484.

Example 7: Strains Expressing β-Glucosidase with the PKL Pathway and Glucoamylase An ABG54 coding sequence, identical to that in plasmid pYKH1127, flanked by the *S. cerevisiae* FBA1 promoter and GPD1 terminator, was integrated at the JIP5 locus in *S. cerevisiae*. The amplified DNA fragment was used as a donor DNA for CRISPR-mediated integration at the JIP5 locus in two parental strains: (i) FG-PKL and (ii) FG-PKL-GA. FG-PKL is an engineered FG yeast having a heterologous phosphoketolase (PKL) pathway involving the expression of phosphoketolase (PKL), phosphotransacetylase (PTA) and acetylating acetyl dehydrogenase (AADH), as described in WO2015148272. FG-PKL-GA is the FG-PKL strain further engineered to expresses a variant of *Trichoderma* glucoamylase.

Integration of the ABG54 expression cassette into these strains was confirmed by colony PCR. The resulting strains, along with the parental strains lacking the ABG54 expression cassette, were grown in corn liquefact in serum vials, and their fermentation products analyzed as described in Example 2. The results are shown in Table 7.

TABLE 6

Performance of β-glucosidase expressing yeast strains versus FG in shake flask assays with or without cellobiose

| Strain | ABG54 exp. | Cellobiose added | Ethanol (g/L) | Glycerol (g/L) | Acetate (g/L) | Glucose (g/L) | DP2 (g/L) | DP3 (g/L) |
|---|---|---|---|---|---|---|---|---|
| GKH-0464 | Yes | No | 146.16 | 16.01 | 0.88 | 2.12 | 4.15 | 1.25 |
| GKH-0484 | Yes | No | 143.87 | 16.36 | 0.88 | 4.87 | 4.12 | 1.40 |
| FG | No | No | 142.02 | 16.25 | 0.92 | 5.73 | 4.24 | 1.58 |
| GKH-0464 | Yes | Yes | 147.00 | 16.34 | 0.90 | 2.86 | 4.31 | 1.37 |
| GKH-0484 | Yes | Yes | 143.36 | 16.39 | 0.92 | 7.58 | 4.64 | 1.50 |
| FG | No | Yes | 142.25 | 16.19 | 0.96 | 6.90 | 10.16 | 1.77 |

TABLE 7

Performance of β-glucosidase expressing strains
G3020 and G3014 versus parental strains in vial assays

| Strains | Features | Ethanol (g/L) | Glycerol (g/L) | Acetate (g/L) | Glucose (g/L) | DP2 (g/L) | DP3 (g/L) |
|---|---|---|---|---|---|---|---|
| FG-PKL | PKL pathway | 145.27 | 12.84 | 1.77 | 2.17 | 4.12 | 1.38 |
| G3020 | PKL pathway + ABG54 | 145.87 | 12.61 | 1.69 | 1.48 | 3.18 | 0.84 |
| FG-PKL-GA | PKL pathway + GA | 146.73 | 11.64 | 1.64 | 1.49 | 4.27 | 1.47 |
| G3014 | PKL pathway + GA + ABG54 | 147.40 | 11.75 | 1.43 | 1.46 | 3.61 | 0.99 |

The β-glucosidase-expressing strains G3020 and G3014 resulted in slightly increased ethanol production (<0.5%) compared to their corresponding parental strains. However, G3020 and G3014 resulted in up to almost 13% decreased acetate, as well as decreased DP2 and decreased DP3 compared to their respective parental strains.

Example 8: Hybrid Yeast Strains Expressing β-Glucosidase

The ABG54 expression cassette from plasmid pYKH1127 was amplified by PCR using primers that incorporate regions of homology to a target site at the JEN1 locus in *S. cerevisiae*. The amplified DNA fragment was used as a donor DNA for CRISPR-mediated integration at the JEN1 locus in two parental strains: (i) DGY1-Δ and (ii) DGY1-Δ-GA. DGY1-Δ is a hybrid yeast strain produced by mating two commercially-available parental yeast strains and further modified by deletion of the YJL065c gene encoding Dls1 (see, e.g., WO2018089333). DGY1-Δ-GA is the DGY1-Δ strain further modified to expresses a glucoamylase.

Integration of the ABG54 expression cassette into these strains was confirmed by colony PCR. The resulting strains, along with the parental strains lacking the ABG54 expression cassette, were grown in corn liquefact in shake flasks, and their fermentation products analyzed as described in Example 2. The results are shown in Table 8.

TABLE 8

Performance of β-glucosidase-expressing hybrid strains versus parental strains

| Strain | Features | Ethanol (g/L) | Glycerol (g/L) | Acetate (g/L) | Glucose (g/L) | DP2 (g/L) | DP3 (g/L) |
|---|---|---|---|---|---|---|---|
| DGY1-Δ | Hybrid | 143.64 | 13.41 | 1.62 | 0.23 | 2.89 | 1.25 |
| GKH-0737 | Hybrid + ABG54 | 144.72 | 13.47 | 1.58 | 0.33 | 2.72 | 0.45 |
| DGY1-Δ-GA | Hybrid + GA | 144.17 | 12.69 | 1.36 | 0.34 | 3.15 | 1.24 |
| GKH-0732 | Hybrid + GA + ABG54 | 145.46 | 12.68 | 1.26 | 0.18 | 4.02 | 0.80 |

The β-glucosidase-expressing strains GKH-0737 and GKH-0732 resulted in up to about 0.9% increased ethanol production compared to their corresponding parental strains and up to over 7% decreased acetate, as well as decreased DP3, compared to their respective parental strains.

Example 9: Comparison of ABG54 and FAB with Other β-Glucosidases In Vitro

Following the observation that ABG54 and FAB were the best expressed β-glucosidases in yeast (Example 3), an experiment similar to that described in Example 1 was performed to compare the activity of ABG54 and FAB to other β-glucosidases in the aforementioned whole stillage assay.

As shown in Example 1, ABG54 was the best performing glycosyl hydrolase for releasing glucose from soluble recalcitrant oligosaccharides in whole stillage, leading to the impetus to express β-glucosidases in yeast. As shown in Example 3, ABG54 and FAB were shown to be the best expressing β-glucosidases for expression in yeast.

In an essentially a fill-circle experiment summarized by the results shown in Table 9, ABG54 and FAB are demonstrated to be better performing β-glucosidases than both Mg3A and TrBgl1 (the two other β-glucosidases tested in yeast) and superior to a blend of other GH-15 and GH-3 molecules. Notably and not surprisingly, all the enzymes selected and tested, herein, were considered best-in-class, otherwise they would not have been tested.

Regardless, the measurable superior performance of ABG54 and FAB compared to Mg3A and TrBgl1 (in particular) in no way explains the remarkable difference in expression in yeast. The differences in expression of the β-glucosidases are ordinals of magnitude greater than the difference in performance of the enzymes in vitro. These data confirm the tenet that expression of exogenous enzymes in yeast is often problematic, and that ABG54 and FAB are especially well expressed, and are additionally superior within their class. These results are shown in Table 9.

TABLE 9

Comparison of in vitro performance
of β-glucosidases expressed in yeast

| Enzyme combination | Glucose produced (mM) |
|---|---|
| PB + ABG54 | 5.99 |
| PB + FAB | 5.61 |
| PB + Mg3A | 4.92 |
| PB + TrBgl1 | 5.49 |
| GH15 + GH3 blend | 3.61 |

What is claimed is:

1. Modified yeast cells derived from parental yeast cells, the modified yeast cells comprising a genetic alteration that causes the modified yeast cells to produce an increased amount of β-glucosidase polypeptides compared to the parental yeast cells, wherein the modified yeast cells produce during fermentation more ethanol and/or less acetate compared to the amount of ethanol and acetate produced by otherwise identical parental yeast cells, wherein the genetic alteration comprises introduction of an expression cassette for expressing a β-glucosidase polypeptide, and wherein the β-glucosidase polypeptides have:
   a) an amino acid sequence having at least 80% amino acid sequence identity to SEQ ID NO: 1 or SEQ ID NO: 2;
   b) the amino acid sequence of a mature polypeptide encoded by a nucleic acid having at least 80% nucleic acid sequence identity to any of SEQ ID NOs: 11-16; or
   c) the amino acid sequence of a mature polypeptide encoded by a nucleic acid that hydridizes, under stringent hybridization conditions comprising 65° C. and 0.1×SSC, to any of SEQ ID NOs: 11-16, or the complement, thereof.

2. The modified yeast cells of claim 1, further comprising an exogenous gene encoding a carbohydrate processing enzyme, wherein the carbohydrate processing enzyme is a dehydrogenase, a transketolase, a phosphoketolase, a transaldolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase, or a laccase.

3. The modified yeast cells of claim 1, further comprising an exogenous PKL pathway.

4. The modified yeast cells of claim 1, further comprising a reduction or elimination of an endogenous NAD-dependent 3-phosphate dehydrogenase (GPD); a disruption of one or more of genes GPD1, GPD2, GPP1, and/or GPP2; overexpression of glycerol dehydrogenase (GCY1); and/or overexpression of dihydroxyacetone kinase (DAK1).

5. The modified yeast cells of claim 1, wherein the modified yeast cells further make reduced amounts of DP2 and/or DP3 compared to otherwise identical parental yeast cells.

6. The modified yeast cells of claim 1, wherein the β-glucosidase polypeptides are derived from *Glomerella graminicola*.

7. The modified yeast cells of claim 1, wherein the cells are of a *Saccharomyces* spp.

8. A method for increasing the production of alcohol and/or decreasing the production of acetate from yeast cells grown on a carbohydrate substrate, comprising: introducing into parental yeast cells a genetic alteration that increases the production of β-glucosidase polypeptides compared to the amount produced in the parental yeast cells, wherein the cells having the introduced genetic alteration are the modified yeast cells of claim 1.

9. The method of claim 8, wherein the increased production of alcohol is at least 0.5%, at least 1.0%, at least 2.0% or at least 3.0%.

10. The method of claim 8, wherein the decreased production of acetate is at least 1.0%, at least 2.0%, at least 4.0% or at least 6.0%.

11. The method of claim 8, wherein the modified yeast cells further comprise an exogenous PKL pathway.

12. The modified yeast cells of claim 1, further comprising a heterologous acetyl-CoA synthase gene and/or increased expression of an endogenous acetyl-CoA synthase gene.

* * * * *

SEQUENCE LISTING

<160> NUMBER OF SEQ ID NOS: 20

<210> SEQ ID NO 1
<211> LENGTH: 860
<212> TYPE: PRT
<213> ORGANISM: Gomerella graminicola

<400> SEQUENCE: 1

```
Ala Val Thr Thr Glu Arg Gln Leu His Lys Arg Asp Leu Ala Tyr Ser
1               5                   10                  15

Pro Pro Val Tyr Pro Ser Pro Trp Met Asp Pro Asn Ala Asp Gly Trp
            20                  25                  30

Thr Asp Ala Tyr Ala Lys Ala Lys Asp Phe Val Ser Gln Leu Thr Leu
        35                  40                  45

Leu Glu Lys Val Asn Leu Thr Thr Gly Val Gly Trp Gln Gly Asp Leu
50                  55                  60

Cys Val Gly Asn Val Gly Ser Val Pro Arg Leu Gly Leu Arg Gly Leu
65                  70                  75                  80

Cys Met Gln Asp Gly Pro Val Gly Ile Arg Phe Ser Asp Tyr Asn Ser
                85                  90                  95

Val Phe Pro Ser Gly Gln Thr Ala Ala Ala Thr Trp Asp Arg Glu Leu
            100                 105                 110

Ile Tyr Arg Arg Ala Glu Ala Ile Gly Phe Glu His Arg Ala Lys Gly
        115                 120                 125

Val Asp Val Val Leu Ala Pro Val Ala Gly Pro Ile Gly Arg Ala Pro
130                 135                 140

Ala Gly Gly Arg Asn Trp Glu Gly Phe Ser Ser Asp Pro Tyr Leu Thr
145                 150                 155                 160

Gly Val Ala Met Ala Glu Ser Val Lys Gly Ile Gln His Ala Ile
                165                 170                 175

Ala Cys Ala Lys His Phe Ile Gly Asn Glu Gln Glu His Phe Arg Gln
                180                 185                 190

Ala Pro Glu Ala Ile Gly Tyr Asn Tyr Thr Ile Asp Glu Ser Ile Ser
            195                 200                 205

Ser Asn Ile Asp Asp Lys Thr Leu His Glu Leu Tyr Leu Trp Pro Phe
210                 215                 220

Gln Asp Ala Val Ala Ala Gly Val Gly Ser Phe Met Cys Ser Tyr Asn
225                 230                 235                 240

Gln Val Asn Asn Ser Tyr Gly Cys Gln Asn Ser Lys Leu Met Asn Gly
                245                 250                 255

Ile Leu Lys Asp Glu Leu Gly Phe Gln Gly Phe Ile Met Ser Asp Trp
            260                 265                 270

Ala Ala Gln His Ala Gly Val Ala Thr Ala Val Ala Gly Leu Asp Met
        275                 280                 285

Ala Met Pro Gly Asp Thr Ala Phe Asn Ser Gly Met Thr Phe Trp Gly
290                 295                 300

Thr Asn Leu Thr Val Ala Val Leu Asn Gly Thr Leu Pro Glu Tyr Arg
305                 310                 315                 320

Leu Asp Asp Met Ala Met Arg Ile Met Ala Ala Phe Phe Lys Val Gly
                325                 330                 335

Phe Glu Leu Asn Glu Val Pro Glu Ile Asn Phe Ser Ser Trp Thr Thr
            340                 345                 350

Asp Thr Val Gly Pro Leu Gln Tyr Tyr Ala Lys Glu Asn Val Gln Val
        355                 360                 365
```

```
Ile Asn Gln His Val Asp Val Arg Arg Gly Gln Glu His Gly Lys Leu
        370                 375                 380
Ile Arg Glu Ile Ala Ala Lys Ala Thr Val Leu Leu Lys Asn Glu Gly
385                 390                 395                 400
Ala Leu Pro Leu Lys Lys Pro Lys Phe Leu Ala Val Ile Gly Glu Asp
                405                 410                 415
Ala Gly Pro Asn Leu Ser Gly Pro Asn Gly Cys Ser Asp His Gly Cys
                420                 425                 430
Asn Glu Gly Thr Leu Gly Ala Gly Trp Gly Ser Gly Thr Ser Asn Tyr
                435                 440                 445
Pro Tyr Leu Ile Thr Pro Asp Gln Ala Leu Gln Ala Arg Ala Val Ala
450                 455                 460
Glu Gly Ser Arg Tyr Glu Ser Ile Leu Ser Asn Tyr Asp Phe Ala Ala
465                 470                 475                 480
Thr Thr Ala Leu Val Thr Gln Pro Asp Ala Thr Ala Ile Val Phe Val
                485                 490                 495
Asn Ala Asp Ser Gly Glu Gly Tyr Ile Asp Val Gly Gly Asn Glu Gly
                500                 505                 510
Asp Arg Gln Asn Leu Thr Leu Trp Asn Gly Gly Asp Glu Leu Val Lys
                515                 520                 525
Asn Val Ala Ala Gly Asn Asn Asn Thr Ile Val Val Ile His Ser Val
530                 535                 540
Gly Pro Val Leu Leu Ala Asp Met Lys Asn Asn Pro Asn Ile Thr Ala
545                 550                 555                 560
Ile Val Trp Ala Gly Leu Pro Gly Gln Glu Ser Gly Asn Ser Ile Thr
                565                 570                 575
Asp Val Leu Tyr Gly Asp Val Asn Pro Gly Gly Lys Ser Pro Phe Thr
                580                 585                 590
Trp Gly Pro Thr Arg Glu Ser Tyr Gly Thr Asp Val Leu Tyr Glu Pro
                595                 600                 605
Asn Asn Gly Glu Gly Ala Pro Gln Asp Asp Phe Ser Glu Gly Val Phe
610                 615                 620
Ile Asp Tyr Arg Tyr Phe Asp Arg Ala Thr Ser Gly Ser Asn Glu Thr
625                 630                 635                 640
Ser Thr Gly Ala Ala Pro Val Tyr Pro Phe Gly Phe Gly Leu Ser Tyr
                645                 650                 655
Thr Thr Phe Glu Tyr Ser Asn Leu Val Val Thr Pro Lys Glu Ala Gly
                660                 665                 670
Glu Tyr Thr Pro Thr Thr Gly Val Thr Glu Lys Ala Pro Thr Phe Gly
                675                 680                 685
Asn Tyr Ser Thr Asp Pro Ala Ala Tyr Val Phe Pro Ser Gly Glu Phe
690                 695                 700
Arg Tyr Ile Tyr Asn Phe Ile Tyr Pro Tyr Leu Asn Thr Thr Asp Ile
705                 710                 715                 720
Ser Lys Ser Ala Asn Asp Pro Ala Tyr Gly Gln Thr Ala Asp Glu Phe
                725                 730                 735
Leu Pro Pro Lys Ala Leu Glu Ser Gly Pro Gln Pro Lys His Pro Ala
                740                 745                 750
Ser Gly Ala Pro Gly Gly Asn Pro Gln Leu Trp Asp Val Leu Tyr Thr
                755                 760                 765
Val Thr Ala Thr Ile Thr Asn Lys Gly Asp Val Ala Gly Asp Glu Val
770                 775                 780
Ala Gln Leu Tyr Val Ser Leu Gly Gly Pro Asn Asp Pro Val Lys Val
```

```
                785                 790                 795                 800
Leu Arg Gly Phe Asp Arg Ile Gly Ile Ala Pro Gly Glu Ser Ala Thr
                805                 810                 815

Phe Thr Ala Asp Ile Thr Arg Arg Asp Leu Ser Asn Trp Asp Thr Val
                820                 825                 830

Ser Gln Asn Trp Val Ile Ser Lys Tyr Pro Lys Lys Val Trp Val Gly
                835                 840                 845

Gly Ser Ser Arg Glu Leu Pro Leu Ser Ala Ser Leu
                850                 855                 860

<210> SEQ ID NO 2
<211> LENGTH: 867
<212> TYPE: PRT
<213> ORGANISM: Artificial Sequence
<220> FEATURE:
<223> OTHER INFORMATION: hybrid from Fusarium vesticilloies / Rasamsonia
      emersonii / Hypocrea jecorina

<400> SEQUENCE: 2

Ala Val Ala Leu Ala Ser Ala Val Pro Asp Thr Leu Ala Gly Val Lys
1               5                   10                  15

Lys Ala Asp Ala Gln Lys Val Val Thr Arg Asp Thr Leu Ala Tyr Ser
                20                  25                  30

Pro Pro His Tyr Pro Ser Pro Trp Met Asp Pro Asn Ala Val Gly Trp
            35                  40                  45

Glu Glu Ala Tyr Ala Lys Ala Lys Ser Phe Val Ser Gln Leu Thr Leu
        50                  55                  60

Met Glu Lys Val Asn Leu Thr Thr Gly Val Gly Trp Gln Gly Glu Arg
65                  70                  75                  80

Cys Val Gly Asn Val Gly Ser Ile Pro Arg Leu Gly Met Arg Gly Leu
                85                  90                  95

Cys Leu Gln Asp Gly Pro Leu Gly Ile Arg Leu Ser Asp Tyr Asn Ser
            100                 105                 110

Ala Phe Pro Ala Gly Thr Thr Ala Gly Ala Ser Trp Ser Lys Ser Leu
        115                 120                 125

Trp Tyr Glu Arg Gly Leu Leu Met Gly Thr Glu Phe Lys Glu Lys Gly
    130                 135                 140

Ile Asp Ile Ala Leu Gly Pro Ala Thr Gly Pro Leu Gly Arg Thr Ala
145                 150                 155                 160

Ala Gly Gly Arg Asn Trp Glu Gly Phe Thr Val Asp Pro Tyr Met Ala
                165                 170                 175

Gly His Ala Met Ala Glu Ala Val Lys Gly Ile Gln Asp Ala Gly Val
            180                 185                 190

Ile Ala Cys Ala Lys His Tyr Ile Ala Asn Glu Gln Glu His Phe Arg
        195                 200                 205

Gln Ser Gly Glu Val Gln Ser Arg Lys Tyr Asn Ile Ser Glu Ser Leu
    210                 215                 220

Ser Ser Asn Leu Asp Asp Lys Thr Met His Glu Leu Tyr Ala Trp Pro
225                 230                 235                 240

Phe Ala Asp Ala Val Arg Ala Gly Val Gly Ser Val Met Cys Ser Tyr
                245                 250                 255

Asn Gln Ile Asn Asn Ser Tyr Gly Cys Gln Asn Ser Lys Leu Leu Asn
            260                 265                 270

Gly Ile Leu Lys Asp Glu Met Gly Phe Gln Gly Phe Val Met Ser Asp
        275                 280                 285
```

```
Trp Ala Ala Gln His Thr Gly Ala Ala Ser Ala Val Ala Gly Leu Asp
290                 295                 300
Met Ser Met Pro Gly Asp Thr Ala Phe Asp Ser Gly Tyr Ser Phe Trp
305                 310                 315                 320
Gly Gly Asn Leu Thr Leu Ala Val Ile Asn Gly Thr Val Pro Ala Trp
                325                 330                 335
Arg Val Asp Asp Met Ala Leu Arg Ile Met Ser Ala Phe Phe Lys Val
                340                 345                 350
Gly Lys Thr Ile Glu Asp Leu Pro Asp Ile Asn Phe Ser Ser Trp Thr
            355                 360                 365
Arg Asp Thr Phe Gly Phe Val His Thr Phe Ala Gln Glu Asn Arg Glu
370                 375                 380
Gln Val Asn Phe Gly Val Asn Val Gln His Asp His Lys Ser His Ile
385                 390                 395                 400
Arg Glu Ala Ala Ala Lys Gly Ser Val Val Leu Lys Asn Thr Gly Ser
                405                 410                 415
Leu Pro Leu Lys Asn Pro Lys Phe Leu Ala Val Ile Gly Glu Asp Ala
                420                 425                 430
Gly Pro Asn Pro Ala Gly Pro Asn Gly Cys Gly Asp Arg Gly Cys Asp
                435                 440                 445
Asn Gly Thr Leu Ala Met Ala Trp Gly Ser Gly Thr Ser Gln Phe Pro
450                 455                 460
Tyr Leu Ile Thr Pro Asp Gln Gly Leu Ser Asn Arg Ala Thr Gln Asp
465                 470                 475                 480
Gly Thr Arg Tyr Glu Ser Ile Leu Thr Asn Asn Glu Trp Ala Ser Val
                485                 490                 495
Gln Ala Leu Val Ser Gln Pro Asn Val Thr Ala Ile Val Phe Ala Asn
                500                 505                 510
Ala Asp Ser Gly Glu Gly Tyr Ile Glu Val Asp Gly Asn Phe Gly Asp
                515                 520                 525
Arg Lys Asn Leu Thr Leu Trp Gln Gln Gly Asp Glu Leu Ile Lys Asn
530                 535                 540
Val Ser Ser Ile Cys Pro Asn Thr Ile Val Leu His Thr Val Gly Pro
545                 550                 555                 560
Pro Val Leu Leu Ala Asp Tyr Glu Lys Asn Pro Asn Ile Thr Ala Ile
                565                 570                 575
Val Trp Ala Gly Leu Pro Gly Gln Glu Ser Gly Asn Ala Ile Ala Asp
                580                 585                 590
Leu Leu Tyr Gly Lys Val Ser Pro Gly Arg Ser Pro Phe Thr Trp Gly
                595                 600                 605
Arg Thr Arg Glu Ser Tyr Gly Thr Glu Val Leu Tyr Glu Ala Asn Asn
610                 615                 620
Gly Arg Gly Ala Pro Gln Asp Asp Phe Ser Glu Gly Val Phe Ile Asp
625                 630                 635                 640
Tyr Arg His Phe Asp Lys Tyr Asn Ile Thr Pro Ile Tyr Glu Phe Gly
                645                 650                 655
His Gly Leu Ser Trp Ser Thr Phe Lys Phe Ser Asn Leu His Ile Gln
                660                 665                 670
Lys Asn Asn Val Gly Pro Met Ser Pro Asn Gly Lys Thr Ile Ala
                675                 680                 685
Ala Pro Ser Leu Gly Asn Phe Ser Lys Asn Leu Lys Asp Tyr Gly Phe
690                 695                 700
Pro Lys Asn Val Arg Arg Ile Lys Glu Phe Ile Tyr Pro Tyr Leu Asn
```

```
                705                 710                 715                 720
Thr Thr Thr Ser Gly Lys Glu Ala Ser Gly Asp Ala His Tyr Gly Gln
                725                 730                 735
Thr Ala Lys Glu Phe Leu Pro Ala Gly Ala Leu Asp Gly Ser Pro Gln
                740                 745                 750
Pro Arg Ser Ala Ala Ser Gly Glu Pro Gly Gly Asn Arg Gln Leu Tyr
                755                 760                 765
Asp Ile Leu Tyr Thr Val Thr Ala Thr Ile Thr Asn Thr Gly Ser Val
                770                 775                 780
Met Asp Asp Ala Val Pro Gln Leu Tyr Leu Ser His Gly Gly Pro Asn
785                 790                 795                 800
Glu Pro Pro Lys Val Leu Arg Gly Phe Asp Arg Ile Glu Arg Ile Ala
                805                 810                 815
Pro Gly Gln Ser Val Thr Phe Lys Ala Asp Leu Thr Arg Arg Asp Leu
                820                 825                 830
Ser Asn Trp Asp Thr Lys Lys Gln Gln Trp Val Ile Thr Asp Tyr Pro
                835                 840                 845
Lys Thr Val Tyr Val Gly Ser Ser Arg Asp Leu Pro Leu Ser Ala
                850                 855                 860
Arg Leu Pro
865

<210> SEQ ID NO 3
<211> LENGTH: 855
<212> TYPE: PRT
<213> ORGANISM: Magnaporthe grisea

<400> SEQUENCE: 3

His Pro Gly Asp Tyr Ser Lys Leu Glu Arg Arg Ala Val Ala Thr Ser
1               5                   10                  15
Glu Pro His Tyr Pro Gln Pro Trp Met Asn Pro Asp Ala Asp Gly Trp
                20                  25                  30
Gln Glu Ala Tyr Val Lys Ala Lys Asp Phe Val Ser Gln Met Thr Leu
            35                  40                  45
Leu Glu Lys Val Asn Leu Thr Thr Gly Val Gly Trp Ala Ser Asp Leu
        50                  55                  60
Cys Val Gly Asn Val Gly Ala Val Pro Arg Leu Gly Leu Arg Ser Leu
65                  70                  75                  80
Cys Leu Gln Asp Ser Pro Thr Gly Val Arg Phe Ala Asp Trp Val Ser
                85                  90                  95
Val Phe Pro Ala Gly Ile Thr Thr Gly Ala Thr Phe Asp Lys Gly Leu
                100                 105                 110
Met Tyr Arg Arg Gly Gln Ala Met Gly Gln Glu Ala Lys Asp Lys Gly
            115                 120                 125
Ile Asn Val Leu Leu Gly Pro Val Ala Gly Leu Gly Arg Val Ala
        130                 135                 140
Ala Gly Gly Arg Ala Trp Glu Ser Phe Gly Ala Asp Pro Val Leu Thr
145                 150                 155                 160
Gly Tyr Gly Met Ile Glu Thr Ile Lys Gly Ile Gln Asp Thr Gly Val
                165                 170                 175
Ile Ala Thr Ala Lys His Phe Ile Gly Asn Glu Gln Glu His Phe Arg
                180                 185                 190
Gln Val Gly Glu Glu Arg Gly Arg Gly Val Asn Ile Ser Glu Ser Leu
            195                 200                 205
```

```
Ser Ser Asn Ile Asp Asp Lys Thr Met His Glu Leu Tyr Leu Trp Pro
210                 215                 220

Phe Ala Asp Ala Val Arg Ala Gly Val Gly Ser Val Met Cys Ser Tyr
225                 230                 235                 240

Thr Gln Val Asn Asn Ser Tyr Gly Cys Gln Asn Ser Lys Leu Leu Asn
                245                 250                 255

Gly Leu Leu Lys Asp Glu Leu Gly Phe Gln Gly Phe Val Met Ser Asp
            260                 265                 270

Trp Gln Ala Gln His Thr Gly Ala Ser Ala Ala Gly Leu Asp
        275                 280                 285

Met Ser Met Pro Gly Asp Thr Glu Phe Asn Thr Gly Leu Ser Phe Trp
290                 295                 300

Gly Ala Asn Leu Thr Leu Ala Val Val Asn Gly Thr Val Ala Glu Trp
305                 310                 315                 320

Arg Ile Asp Asp Met Ala Met Arg Ile Met Ala Ala Phe Phe Lys Val
                325                 330                 335

Gly Asn Thr Leu Asp Gln Pro Glu Ile Asn Phe Ser Ser Trp Thr Lys
            340                 345                 350

Asp Thr Phe Gly Pro Leu His Ser Ser Gly Asn Arg Ile Gln Gln
        355                 360                 365

Ile Asn Gln His Val Asp Val Arg Arg Asp His Gly Asn Leu Ile Arg
370                 375                 380

Glu Val Ala Ala Lys Gly Thr Val Leu Leu Lys Asn Thr Asn Asn Ala
385                 390                 395                 400

Leu Pro Leu Asn Lys Pro Lys Phe Leu Ala Val Ile Gly Asp Asp Ala
                405                 410                 415

Gly Ser Asn Pro Arg Gly Pro Asn Gly Cys Pro Asp Arg Gly Cys Leu
            420                 425                 430

Leu Gly Thr Leu Gly Met Ala Trp Gly Ser Gly Thr Ala Asp Phe Pro
        435                 440                 445

Tyr Leu Ile Thr Pro Asp Ala Ala Leu Gln Ala Gln Ala Ile Glu Asp
    450                 455                 460

Gly Thr Arg Tyr Glu Ser Ile Leu Ser Asn Tyr Ala Thr Ala Gln Thr
465                 470                 475                 480

Gln Ala Leu Val Ser Gln Thr Tyr Ala Thr Ala Ile Val Phe Val Ala
                485                 490                 495

Ala Ser Ser Gly Glu Gly Tyr Ile Asp Phe Asp Gly Asn Lys Gly Asp
            500                 505                 510

Arg Asn Asn Leu Thr Leu Trp Tyr Asp Gly Asp Ser Leu Val Lys Asn
        515                 520                 525

Val Ser Ser Val Cys Asn Asn Thr Ile Val Val Ile His Ser Thr Gly
    530                 535                 540

Pro Thr Ile Leu Thr Glu Trp Tyr Asp Asn Pro Asn Val Thr Ala Ile
545                 550                 555                 560

Val Trp Ala Gly Val Pro Gly Gln Glu Ser Gly Arg Ala Ile Thr Asp
                565                 570                 575

Val Leu Tyr Gly Arg Val Asn Pro Ala Gly Arg Ser Pro Phe Thr Trp
            580                 585                 590

Gly Lys Thr Arg Glu Ser Tyr Gly Thr Asp Val Met Tyr Lys Pro Asn
        595                 600                 605

Asn Gly Asn Glu Ala Pro Gln Gln Asp Tyr Thr Glu Gly Val Phe Ile
    610                 615                 620

Asp Tyr Arg His Phe Asp Gln Gln Lys Asp Glu Pro Val Tyr Glu Phe
```

```
                625                 630                 635                 640
Gly His Gly Leu Ser Tyr Thr Thr Phe Glu Tyr Ser Asn Ile Arg Val
                        645                 650                 655

Asp Lys Ala Pro Ala Ser Glu Tyr Lys Pro Thr Thr Gly Gln Thr Ile
                660                 665                 670

Pro Ala Pro Val Phe Gly Ala Asn Val Ser Lys Asp Leu Ser Gln Tyr
            675                 680                 685

Thr Phe Pro Ser Asp Glu Phe Pro His Ile Tyr Leu Phe Ile Tyr Pro
        690                 695                 700

Tyr Leu Asn Thr Ser Ser Gly Glu Glu Ala Ser Arg Asp Pro Lys
705                 710                 715                 720

Tyr Gly Gly Thr Ala Glu Glu Phe Leu Pro Lys Ala Leu Asp Gly
                    725                 730                 735

Ser Pro Gln Pro Leu Pro Arg Ala Ser Gly Lys Asn Ser Pro Gly Gly
                740                 745                 750

Asn Arg Gln Leu Tyr Asp Thr Leu Tyr Thr Val Thr Ala Thr Ile Thr
                    755                 760                 765

Asn Thr Gly Lys Leu Val Gly Glu Val Pro Gln Leu Tyr Val Ser
770                 775                 780

His Gly Gly Pro Glu Asp Pro Pro Val Val Leu Arg Gly Phe Glu Arg
785                 790                 795                 800

Ile Arg Leu Asp Pro Gly Gln Ser Ala Thr Phe Lys Val Asp Leu Thr
                        805                 810                 815

Arg Arg Asp Val Ser Asn Trp Asp Val Lys Val Gln Asp Trp Val Ile
                820                 825                 830

Ser Glu His Pro Lys Lys Val Phe Val Gly Ser Ser Arg Lys Leu
                    835                 840                 845

His Leu Ser Ala Asp Leu Asn
        850                 855

<210> SEQ ID NO 4
<211> LENGTH: 521
<212> TYPE: PRT
<213> ORGANISM: Hypocrea jecorina

<400> SEQUENCE: 4

Asp Ser His Ser Thr Ser Gly Ala Ser Ala Glu Ala Val Val Pro Pro
1               5                   10                  15

Ala Gly Thr Pro Trp Gly Thr Ala Tyr Asp Lys Ala Lys Ala Ala Leu
                20                  25                  30

Ala Lys Leu Asn Leu Gln Asp Lys Val Gly Ile Val Ser Gly Val Gly
            35                  40                  45

Trp Asn Gly Gly Pro Cys Val Gly Asn Thr Ser Pro Ala Ser Lys Ile
        50                  55                  60

Ser Tyr Pro Ser Leu Cys Leu Gln Asp Gly Pro Leu Gly Val Arg Tyr
65                  70                  75                  80

Ser Thr Gly Ser Thr Ala Phe Thr Pro Gly Val Gln Ala Ala Ser Thr
                85                  90                  95

Trp Asp Val Asn Leu Ile Arg Glu Arg Gly Gln Phe Ile Gly Glu Glu
            100                 105                 110

Val Lys Ala Ser Gly Ile His Val Ile Leu Gly Pro Val Ala Gly Pro
        115                 120                 125

Leu Gly Lys Thr Pro Gln Gly Gly Arg Asn Trp Glu Gly Phe Gly Val
    130                 135                 140
```

```
Asp Pro Tyr Leu Thr Gly Ile Ala Met Gly Gln Thr Ile Asn Gly Ile
145                 150                 155                 160

Gln Ser Val Gly Val Gln Ala Thr Ala Lys His Tyr Ile Leu Asn Glu
            165                 170                 175

Gln Glu Leu Asn Arg Glu Thr Ile Ser Ser Asn Pro Asp Asp Arg Thr
        180                 185                 190

Leu His Glu Leu Tyr Thr Trp Pro Phe Ala Asp Ala Val Gln Ala Asn
    195                 200                 205

Val Ala Ser Val Met Cys Ser Tyr Asn Lys Val Asn Thr Thr Trp Ala
210                 215                 220

Cys Glu Asp Gln Tyr Thr Leu Gln Thr Val Leu Lys Asp Gln Leu Gly
225                 230                 235                 240

Phe Pro Gly Tyr Val Met Thr Asp Trp Asn Ala Gln His Thr Thr Val
                245                 250                 255

Gln Ser Ala Asn Ser Gly Leu Asp Met Ser Met Pro Gly Thr Asp Phe
            260                 265                 270

Asn Gly Asn Asn Arg Leu Trp Gly Pro Ala Leu Thr Asn Ala Val Asn
        275                 280                 285

Ser Asn Gln Val Pro Thr Ser Arg Val Asp Asp Met Val Thr Arg Ile
    290                 295                 300

Leu Ala Ala Trp Tyr Leu Thr Gly Gln Asp Gln Ala Gly Tyr Pro Ser
305                 310                 315                 320

Phe Asn Ile Ser Arg Asn Val Gln Gly Asn His Lys Thr Asn Val Arg
                325                 330                 335

Ala Ile Ala Arg Asp Gly Ile Val Leu Leu Lys Asn Asp Ala Asn Ile
            340                 345                 350

Leu Pro Leu Lys Lys Pro Ala Ser Ile Ala Val Val Gly Ser Ala Ala
        355                 360                 365

Ile Ile Gly Asn His Ala Arg Asn Ser Pro Ser Cys Asn Asp Lys Gly
    370                 375                 380

Cys Asp Asp Gly Ala Leu Gly Met Gly Trp Gly Ser Gly Ala Val Asn
385                 390                 395                 400

Tyr Pro Tyr Phe Val Ala Pro Tyr Asp Ala Ile Asn Thr Arg Ala Ser
                405                 410                 415

Ser Gln Gly Thr Gln Val Thr Leu Ser Asn Thr Asp Asn Thr Ser Ser
            420                 425                 430

Gly Ala Ser Ala Ala Arg Gly Lys Asp Val Ala Ile Val Phe Ile Thr
        435                 440                 445

Ala Asp Ser Gly Glu Gly Tyr Ile Thr Val Glu Gly Asn Ala Gly Asp
    450                 455                 460

Arg Asn Asn Leu Asp Pro Trp His Asn Gly Asn Ala Leu Val Gln Ala
465                 470                 475                 480

Val Ala Gly Ala Asn Ser Asn Val Ile Val Val His Ser Val Gly
                485                 490                 495

Ala Ile Ile Leu Glu Gln Ile Leu Ala Leu Pro Gln Val Lys Ala Val
            500                 505                 510

Val Trp Ala Gly Leu Pro Ser Gln Glu
        515                 520

<210> SEQ ID NO 5
<211> LENGTH: 19
<212> TYPE: PRT
<213> ORGANISM: Gomerella graminicola

<400> SEQUENCE: 5
```

```
Met Arg Ser Gln Thr Leu Ala Val Ala Leu Leu Ala Ala Ala Asp Gln
1               5                   10                  15

Val Ala Ala
```

<210> SEQ ID NO 6
<211> LENGTH: 19
<212> TYPE: PRT
<213> ORGANISM: Fusarium vesticilloies

<400> SEQUENCE: 6

```
Met Lys Leu Asn Trp Val Ala Ala Ala Leu Ser Ile Gly Ala Ala Gly
1               5                   10                  15

Thr Asp Ser
```

<210> SEQ ID NO 7
<211> LENGTH: 18
<212> TYPE: PRT
<213> ORGANISM: Magnaporthe grisea

<400> SEQUENCE: 7

```
Met Arg Phe Ser Gly Ile Val Ala Thr Leu Val Ala Gly Ala Gly Val
1               5                   10                  15

Ser Ala
```

<210> SEQ ID NO 8
<211> LENGTH: 19
<212> TYPE: PRT
<213> ORGANISM: Hypocrea jecorina

<400> SEQUENCE: 8

```
Met Arg Tyr Arg Thr Ala Ala Ala Leu Ala Leu Ala Thr Gly Pro Phe
1               5                   10                  15

Ala Arg Ala
```

<210> SEQ ID NO 9
<211> LENGTH: 85
<212> TYPE: PRT
<213> ORGANISM: Saccharomyces cerevisiae

<400> SEQUENCE: 9

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Asp Lys Arg
                85
```

<210> SEQ ID NO 10
<211> LENGTH: 19
<212> TYPE: PRT
<213> ORGANISM: Saccharomyces cerevisiae

<400> SEQUENCE: 10

Met Leu Leu Gln Ala Phe Leu Phe Leu Leu Ala Gly Phe Ala Ala Lys
1               5                   10                  15

Ile Ser Ala

<210> SEQ ID NO 11
<211> LENGTH: 2640
<212> TYPE: DNA
<213> ORGANISM: Artificial Sequence
<220> FEATURE:
<223> OTHER INFORMATION: synthetic DNA

<400> SEQUENCE: 11

| | | | | | |
|---|---|---|---|---|---|
| atgagatctc | agacattagc | ggtagcacta | ttggcggcag | cggaccaggt | tgcagcagca | 60 |
| gtaacaactg | agagacaact | acataagaga | gacttggctt | attctccacc | tgtttacccc | 120 |
| tctccgtgga | tggaccctaa | tgctgacggt | tggacggatg | cttatgctaa | agctaaggat | 180 |
| ttcgtaagcc | aactgacgct | gttagagaag | gtaaacctaa | cgactggcgt | cggatggcag | 240 |
| ggtgatctat | gtgtagggaa | cgtggggagc | gtgccaaggc | tggggctaag | aggtctgtgc | 300 |
| atgcaagatg | gtcccgtagg | aatacgtttc | agcgactaca | actctgtctt | tccttcaggt | 360 |
| caaacggcag | cggccacatg | ggacagagag | cttatttacc | gtagggcgga | agcaatcggt | 420 |
| tttgaacaca | gggcgaaagg | agtagacgtc | gtcctagccc | cggtcgcagg | gcccataggt | 480 |
| agagccccag | caggggggcag | aaactgggaa | ggattcagtt | cagacccgta | cctgacggga | 540 |
| gtggcgatgg | ccgaatctgt | aaagggaatt | caacaacacg | ccatcgcctg | tgccaaacat | 600 |
| tttataggaa | cgaacagga | gcattttagg | caagcgcccg | aggcaatagg | gtacaattac | 660 |
| actatagacg | aaagcatcag | tagcaacatc | gacgataaaa | cactacatga | attgtactta | 720 |
| tggccattcc | aggacgcagt | ggctgcagga | gtgggctctt | tcatgtgcag | ctataaccaa | 780 |
| gtgaacaact | catacggttg | tcaaaatagc | aaacttatga | atggcatcct | gaaggacgag | 840 |
| ttgggcttcc | aaggtttcat | tatgtctgac | tgggcagcac | aacatgcagg | agtcgctacc | 900 |
| gcggtagccg | gattagatat | ggctatgcct | ggggatacag | cttttaattc | aggcatgacg | 960 |
| ttctggggta | ccaatctaac | agtagccgtc | ttaaatggaa | ctctgcccga | atatagactg | 1020 |
| gatgatatgg | ccatgagaat | tatggcggct | tttttcaaag | tcgggtttga | gctgaatgag | 1080 |
| gtgccggaaa | taaattttag | ctcatggacg | actgacaccg | ttggcccccct | acaatactat | 1140 |
| gcaaaagaga | acgttcaggt | tattaatcag | cacgttgatg | tcagaagagg | ccaagagcac | 1200 |
| ggaaagttga | ttagagaaat | agcggcgaaa | gccactgtct | tgttgaagaa | tgagggagcc | 1260 |
| ttgccgttga | agaagccgaa | gttttttggca | gtgattggcg | aggacgccgg | tcccaacttg | 1320 |
| tctggtccta | cgggtgcag | tgatcatgga | tgtaacgagg | gtaccctagg | cgcaggatgg | 1380 |
| ggatcaggga | cctcaaacta | tccctatcta | atcacccctg | atcaagcgct | acaagcgcgt | 1440 |
| gctgtagcgg | agggttctag | atacgaatct | attctttcaa | attacgactt | tgcggccaca | 1500 |
| acagctcttg | tgacccagcc | tgacgccacc | gctattgtct | tgttaacgc | agattccaggt | 1560 |
| gaagggtata | ttgatgtggg | aggtaacgaa | ggcgacaggc | agaacctgac | gctgtggaac | 1620 |
| ggcggcgatg | agttggtgaa | aaacgttgcc | gcaggtaata | acaataccat | agtagtaatc | 1680 |
| cattcagtag | gtccggtcct | tctggcggat | atgaaaaata | ccctaatat | caccgctatt | 1740 |
| gtatgggctg | gtttgcctgg | acaggagtct | ggaaattcaa | ttactgatgt | tctgtacggg | 1800 |
| gatgtcaacc | ccgagggaa | atccccattc | acgtggggac | ctactcgtga | atcctatggc | 1860 |
| acggacgtcc | tgtacgagcc | aaacaacggt | gaaggggctc | ctcaagatga | ctttagcgaa | 1920 |

```
ggagtgttca tcgattatcg ttactttgat cgtgccacgt ctgggtccaa tgaaacgtcc    1980
acgggtgcgg cgccagttta cccatttggg tttgggcttt cttatactac gtttgagtac    2040
tctaatctgg tcgttacgcc gaaggaagcg ggtgaataca caccaactac tggtgtgact    2100
gagaaggcgc ctacgtttgg gaactacagc accgaccccg ctgcatacgt ctttccctca    2160
ggtgaattca ggtacattta aatttcatt tatccgtacc taaatactac agatatatct    2220
aagtctgcga atgatcctgc gtatgggcag acggccgatg agttcctacc acctaaggcg    2280
cttgagagcg ggccgcagcc aaaacatcct gctagcggtg cccctggggg taatccacaa    2340
ttgtgggacg ttttgtatac cgttaccgcc acgattacga ataaaggaga tgttgccggc    2400
gatgaggttg cccaattgta tgtgtctctg ggaggtccaa tgacccccgt taaggtgcta    2460
agaggttttg acaggattgg gatagctcca ggggaaagtg ccacttttac ggctgacatt    2520
acgcgtcgtg acttgagcaa ctgggacacc gtctcacaaa attgggtgat tagtaaatat    2580
ccaaagaagg tttgggtcgg aggatcatca cgtgagttgc cgctatccgc aagcctatga    2640
```

<210> SEQ ID NO 12
<211> LENGTH: 2838
<212> TYPE: DNA
<213> ORGANISM: Artificial Sequence
<220> FEATURE:
<223> OTHER INFORMATION: synthetic DNA

<400> SEQUENCE: 12

```
atgagattcc catccatctt tactgccgtc ttgttcgccg ctagttccgc tttggctgct      60
ccagttaaca ctactactga agacgaaact gcccaaatcc cagccgaagc cgtcattggt     120
tacttggatt tagaaggtga tttcgatgtt gctgttttgc cattctccaa ctccaccaac     180
aacggtttgc tatttatcaa caccactatc gcttccatcg ctgctaagga ggaaggtgtc     240
tctttggata agagagctgt taccactgaa agacaattac acaagagaga cttagcttac     300
tctcctccag tttacccatc tccatggatg gaccccaaacg ccgacggttg gactgacgct     360
tacgctaagg ctaaggactt cgtctctcaa ttgactttgt tagaaaaggt taacttgacc     420
actggtgtcg gttggcaagg tgacttatgt gtcggtaacg tgggttctgt cccacgtttg     480
ggtctaagag gtttgtgtat gcaagacggt ccagttggta ttagattctc tgactacaac     540 tcagttttc catctggtca aaccgctgcc gccacttggg acagagaatt gatctacaga     600
agagctgaag ctattggttt tgaacacaga gctaagggtg tcgatgtcgt tttggctcca     660
gtcgctggtc caattggcag agctcctgcc ggtggtagaa actgggaagg tttctctagc     720
gacccatact tgactggtgt tgccatggcc gaatctgtca agggtattca acaacacgct     780
atcgcttgtg ctaagcactt cataggtaac gaacaagaac acttcagaca gctcccagaa     840
gctatcggtt acaattacac catcgatgaa tctatttcct ccaacatcga cgataagacc     900
ttgcatgaat gtacttgtg gcctttccaa gatgctgttg ctgctggtgt cggctccttc     960
atgtgttctt acaatcaagt caacaactct tacggttgtc aaaactctaa gttgatgaac    1020
ggtattttga agacgaatt aggtttccaa ggtttcatca tgtctgattg ggctgctcaa    1080
cacgctggtt tgccaccgcc cgttgctggt ttggacatgg ctatgccagg tgacaccgct    1140
tttaactctg gcatgacctt ctggggtact aatttgactg tcgctgttct aaacggtacc    1200
ttgccagaat accgtttgga cgacatggct atgagaatca tggctgcttt cttcaaggtt    1260
ggtttcgaac taaacgaagt tccagaaatt aactttccct cttggactac tgacaccgtc    1320
ggaccattgc aatactacgc taaggaaaac gttcaagtca ttaaccaaca cgttgatgtt    1380
```

```
agaagaggtc aagagcacgg taagttgatc agagaaattg ctgctaaagc caccgtattg    1440
ctaaaaaacg aaggtgcttt gcccttgaag aagccaaagt tcttggctgt catcggtgaa    1500
gatgccggtc caaacttgtc tggtccaaac ggttgctctg atcacggttg taacgaaggt    1560
accttgggtg ctggttgggg ttctggtacc tccaactacc cctacctaat caccccagat    1620
caagctttgc aagctagagc tgtcgctgaa ggttccagat acgaatctat cttgtctaat    1680
tacgacttcg ctgccaccac cgctttggtc acccaaccag acgccacagc tatcgtcttc    1740
gtcaacgctg actccggtga aggttacatc gacgttggtg gtaacgaagg tgacagacaa    1800
aacttgactt tgtggaacgg tggtgacgag ttggtcaaaa acgtcgctgc tggtaataac    1860
aacaccatcg ttgttattca ctctgtaggt ccagtcttgt tagccgatat gaagaacaac    1920
ccaaacatca ccgctatcgt ttgggctggt ttaccaggtc aagaaagtgg taactctatc    1980
actgacgtct tgtacggtga cgtcaacccc ggtggtaagt caccattcac ctggggtccc    2040
actagagaat cctacggtac tgacgtcttg tacgaaccta caacggtga aggtgcccca    2100 caagacgact tctccgaagg tgttttcatc gactacagat acttcgatag ggctacttct    2160
ggttctaatg aaacctccac tggtgccgcc ccagtttacc cattcggttt cggtttgtct    2220
tacaccacct tcgaatactc caacttggtc gttaccccaa aggaggccgg tgaatacact    2280
ccaactactg gtgtcactga aaaggcccct accttcggta actactctac cgacccagct    2340
gcttacgtct tcccatccgg tgaattcaga tacatttaca acttcatcta cccatactta    2400
aacaccactg acatctccaa gtccgccaac gacccagcct acggtcaaac tgccgatgaa    2460
ttcttaccac caaaggcctt ggaaagtggt ccacaaccaa acatccagc ctctggtgct    2520 ccaggtggta atccacaatt gtgggacgtt ttgtacactg tcactgctac catcacaaat    2580
aagggtgacg tcgctggcga cgaagttgct caattatacg tgtctctagg tggtccaaac    2640
gatcctgtca aggttctacg tggtttcgat cgtattggta tcgctcctgg tgaatctgct    2700
actttcaccg ctgacattac cagaagagat ttgtctaact gggacaccgt tagtcaaaac    2760
tgggtcatct ctaagtaccc aaagaaggtt tgggttggtg gttctagcag agaattgcct    2820
ttatctgctt ccttgtaa                                                 2838

<210> SEQ ID NO 13
<211> LENGTH: 2640
<212> TYPE: DNA
<213> ORGANISM: Artificial Sequence
<220> FEATURE:
<223> OTHER INFORMATION: synthetic DNA

<400> SEQUENCE: 13
atgctactcc aagcattcct ttttctgtta gcaggatttg ctgccaaaat ctctgctgca     60
gtaacaactg agagacaact acataagaga gacttggctt attctccacc tgtttacccc    120
tctccgtgga tggaccctaa tgctgacggt tggacggatg cttatgctaa agctaaggat    180
ttcgtaagcc aactgacgct gttagagaag gtaaacctaa cgactggcgt cggatggcag    240
ggtgatctat gtgtagggaa cgtggggagc gtgccaaggc tggggctaag aggtctgtgc    300
atgcaagatg gtcccgtagg aatacgtttc agcgactaca actctgtctt ccttcaggt    360 caaacggcag cggccacatg ggacagagag cttatttacc gtagggcgga agcaatcggt    420
tttgaacaca gggcgaaagg agtagacgtc gtcctagccc cggtcgcagg gcccataggt    480
agagccccag cagggggcag aaactgggaa ggattcagtt cagacccgta cctgacggga    540
```

| | | | |
|---|---|---|---|
| gtggcgatgg | ccgaatctgt | aaagggaatt caacaacacg ccatcgcctg tgccaaacat | 600 |
| tttataggaa | acgaacagga | gcattttagg caagcgcccg aggcaatagg gtacaattac | 660 |
| actatagacg | aaagcatcag | tagcaacatc gacgataaaa cactacatga attgtactta | 720 |
| tggccattcc | aggacgcagt | ggctgcagga gtgggctctt tcatgtgcag ctataaccaa | 780 |
| gtgaacaact | catacggttg | tcaaaatagc aaacttatga atggcatcct gaaggacgag | 840 |
| ttgggcttcc | aaggtttcat | tatgtctgac tgggcagcac aacatgcagg agtcgctacc | 900 |
| gcggtagccg | gattagatat | ggctatgcct ggggatacag cttttaattc aggcatgacg | 960 |
| ttctggggta | ccaatctaac | agtagccgtc ttaaatggaa ctctgcccga atatagactg | 1020 |
| gatgatatgg | ccatgagaat | tatggcggct tttttcaaag tcgggtttga gctgaatgag | 1080 |
| gtgccggaaa | taatttttag | ctcatggacg actgacaccg ttggcccct acaatactat | 1140 |
| gcaaaagaga | acgttcaggt | tattaatcag cacgttgatg tcagaagagg ccaagagcac | 1200 |
| ggaaagttga | ttagagaaat | agcggcgaaa gccactgtct tgttgaagaa tgagggagcc | 1260 |
| ttgccgttga | agaagccgaa | gttttggca gtgattggcg aggacgccgg tcccaacttg | 1320 |
| tctggtccta | acgggtgcag | tgatcatgga tgtaacgagg gtaccctagg cgcaggatgg | 1380 |
| ggatcaggga | cctcaaacta | tccctatcta atcacccctg atcaagcgct acaagcgcgt | 1440 |
| gctgtagcgg | agggttctag | atacgaatct attctttcaa attacgactt tgcggccaca | 1500 |
| acagctcttg | tgacccagcc | tgacgccacc gctattgtct tgttaacgc agattcaggt | 1560 |
| gaagggtata | ttgatgtggg | aggtaacgaa ggcgacaggc agaacctgac gctgtggaac | 1620 |
| ggcggcgatg | agttggtgaa | aaacgttgcc gcaggtaata acaataccat agtagtaatc | 1680 |
| cattcagtag | gtccggtcct | tctggcggat atgaaaaata accctaatat caccgctatt | 1740 |
| gtatgggctg | gtttgcctgg | acaggagtct ggaaattcaa ttactgatgt tctgtacggg | 1800 |
| gatgtcaacc | ccggagggaa | atccccattc acgtggggac ctactcgtga atcctatggc | 1860 |
| acggacgtcc | tgtacgagcc | aaacaacggt gaagggctc ctcaagatga ctttagcgaa | 1920 |
| ggagtgttca | tcgattatcg | ttactttgat cgtgccacgt ctgggtccaa tgaaacgtcc | 1980 |
| acgggtgcgg | cgccagttta | cccatttggg tttgggcttt cttatactac gtttgagtac | 2040 |
| tctaatctgg | tcgttacgcc | gaaggaagcg ggtgaataca caccaactac tggtgtgact | 2100 |
| gagaaggcgc | ctacgtttgg | gaactacagc accgaccccg ctgcatacgt ctttccctca | 2160 |
| ggtgaattca | ggtacattta | taatttcatt tatccgtacc taaatactac agatatatct | 2220 |
| aagtctgcga | atgatcctgc | gtatgggcag acggccgatg agttcctacc acctaaggcg | 2280 |
| cttgagagcg | ggccgcagcc | aaaacatcct gctagcggtg ccctggggg taatccacaa | 2340 |
| ttgtgggacg | ttttgtatac | cgttaccgcc acgattacga ataaaggaga tgttgccggc | 2400 |
| gatgaggttg | cccaattgta | tgtgtctctg ggaggtccaa atgacccgt taaggtgcta | 2460 |
| agaggttttg | acaggattgg | gatagctcca ggggaaagtg ccactttac ggctgacatt | 2520 |
| acgcgtcgtg | acttgagcaa | ctgggacacc gtctcacaaa attgggtgat tagtaaatat | 2580 |
| ccaaagaagg | tttgggtcgg | aggatcatca cgtgagttgc cgctatccgc aagcctatga | 2640 |

<210> SEQ ID NO 14
<211> LENGTH: 2661
<212> TYPE: DNA
<213> ORGANISM: Artificial Sequence
<220> FEATURE:
<223> OTHER INFORMATION: synthetic DNA

<400> SEQUENCE: 14

-continued

```
atgaagctaa actgggtcgc tgcggctcta tctatcggag ctgcaggaac ggatagtgca      60
gtcgctcttg cctccgctgt accagacact cttgctggag taaagaaggc tgacgcccaa     120
aaggtggtta ctagagatac actggcctac tccccaccac actatccctc tccgtggatg     180
gacccaaatg ctgtggggtg ggaggaagcg tatgcgaagg caaagagttt tgtatcccaa     240
cttaccttaa tggaaaaagt gaatttaact acaggagtcg gttggcaagg agaaagatgt     300
gttggcaatg tgggcagtat acccagacta ggcatgaggg gactatgtct tcaggacgga     360
ccgctgggaa ttaggctgtc cgactacaat tcagcgtttc cagctggtac taccgctggg     420
gcgtcatgga gcaaaagtct gtggtacgaa cgtgggctat tgatgggtac tgaatttaag     480
gaaaagggga tcgatatcgc attaggtcct gcgactggac cgttaggcag gaccgccgcc     540
ggtggaagaa attgggaggg atttacggtt gatccgtata tggccggtca tgcaatggcg     600
gaagccgtga aaggcataca agacgccggc gtcatagcct gcgccaagca ctacatagcc     660
aatgaacaag aacattttcg tcaatctgga gaagtccaaa gcagaaagta caacatcagc     720
gaatccctat catccaactt agacgacaag actatgcacg agttatatgc ttggccgttc     780
gccgatgccg tcagctgg a gtaggttct gtcatgtgct cctataacca gattaacaac     840
agttatggat gtcaaaactc caaactactg aatgggatct aaaagatga gatgggtttt     900
caaggctttg taatgtctga ctgggccgcc cagcacactg gtgcggccag tgcagttgca     960
ggactagata tgagtatgcc aggcgataca gcgtttgatt ctggctacag tttctggggt    1020
ggtaatctaa cttttggcagt gatcaatggg acagtaccgg cctggagggt agatgatatg    1080
gcgttgagaa ttatgtccgc gttcttcaag gtgggtaaaa ctatagaaga cctgcctgat    1140
ataaattttt catcttggac aagggatacg tttggattcg tacatacgtt tgcacaagag    1200
aaccgtgaac aagtgaattt tggggtcaac gtacagcacg accacaagag ccacattaga    1260
gaagccgcgg ccaagggatc agtggtgcta aaaaacaccg ggtcccttcc acttaaaaac    1320
ccaaagtttt tagcagtaat aggggaagac gcgggaccaa atcctgctgg tcccaacggc    1380
tgcggagatc gtgggtgtga ataatggaacg cttgctatgg catgggggatc cggcacaagc    1440
cagttcccct atcttatcac ccctgatcaa ggattaagca accgtgccac acaagatggt    1500
accaggtatg aaagcatctt gaccaacaat gagtgggcaa gcgtacaagc gctggtttct    1560
caacccaacg tgcagcaat tgtcttcgca acgctgatt ctggagaagg ttatattgag    1620
gtagatggaa atttcgggga tagaaaaaac ctgaccttgt ggcagcaggg cgacgagctt    1680
ataaagaacg tatcttccat atgtcctaat acgatagtag tcctacatac agtaggtccc    1740
gtcttattag cggactatga gaagaatccc aacatcacag ccatagtttg gcgggttta    1800
ccagggcagg agagtggtaa cgcgatcgcc gatttgctat atggaaaagt ctctccgggc    1860
aggagcccat tcacctgggg aagaacgagg gaatcctatg gcacagaggt actatatgaa    1920
gccaataacg gcagaggcgc accacaagat gactttagcg aagggtcttt catcgattat    1980
cgtcactttg ataaatacaa catcacgccg atatacgagt tcggtcatgg tttatcctgg    2040
agcacattta agttctctaa cctgcacatt cagaagaata acgtcgggcc aatgtcacct    2100
ccaaatggta aaacgatagc tgcaccttcc ttaggaaatt tttccaagaa cctaaaggat    2160
tatggcttcc ccaaaaacgt aagaagaatt aaagagttta tttacccta tctgaacact    2220
actacttccg gaaaggaagc ctcaggtgac gcacattacg ggcaaaccgc caaggaattt    2280
ttgccggcag gtgcgctaga tggttctccg cagccccgtt ccgcagctag cggcgagccc    2340
```

-continued

| | |
|---|---|
| ggtggaaaca gacagctgta tgatatttta tataccgtaa ccgctactat cacaaataca | 2400 |
| ggttcagtta tggatgacgc cgttccccag ctatatctgt cccatggggg gccaaatgaa | 2460 |
| cctccgaaag tgctgagagg ttttgataga atagagagaa ttgcaccggg tcagagcgtt | 2520 |
| actttcaagg cagacttgac cagaagggat ttaagtaact gggatacaaa aaaacaacaa | 2580 |
| tgggtcatca ccgattaccc gaagactgtt tacgttggat caagctccag agacttgccg | 2640 |
| ttaagcgcca gactgccgta g | 2661 |

<210> SEQ ID NO 15
<211> LENGTH: 2859
<212> TYPE: DNA
<213> ORGANISM: Artificial Sequence
<220> FEATURE:
<223> OTHER INFORMATION: synthetic DNA

<400> SEQUENCE: 15

| | |
|---|---|
| atgagattcc catctatctt caccgccgtc ttgttcgctg cctcttctgc tttggctgcc | 60 |
| ccagttaaca ccactactga agatgaaacc gctcaaatcc cagctgaagc tgtcattggt | 120 |
| tacttggact agaaggtga tttcgatgtt gctgttctac cattctctaa ttctaccaac | 180 |
| aacggcttgt tgttcatcaa caccactatc gcttccatcg ctgccaagga agaaggtgtc | 240 |
| tctttggata aaagagctgt cgcttttggc ctctgccgttc cagacactct agccggtgtc | 300 |
| aagaaggctg acgcccaaaa ggtcgtgact agagacactt tggcttacag cccaccacac | 360 |
| tacccatctc cttggatgga cccaaacgct gtcggttggg aagaagccta cgctaaggcc | 420 |
| aagtccttcg tctctcaatt gaccttgatg gaaaaggtca atttaaccac cggtgttggt | 480 |
| tggcaaggtg aaagatgtgt cggtaacgtt ggatccatcc ctagattggg tatgcgtggt | 540 |
| ttgtgtttgc aagacggtcc attgggtatc agattgtctg actacaactc agctttccct | 600 |
| gctggtacta ccgccggtgc ttcttggtct aagtccttgt ggtacgaaag aggtttgttg | 660 |
| atgggtaccg aatttaagga aaagggtatt gatatcgctt gggtcctgc acaggtcct | 720 |
| ttgggtagaa ctgctgctgg tgtagaaac tgggaaggtt tcaccgtcga cccatacatg | 780 |
| gctggccacg ctatggccga agccgttaag ggtatccaag acgctggtgt tatcgcttgt | 840 |
| gctaagcact acattgccaa cgaacaagaa cactttagac aatctggtga agtccaatcc | 900 |
| agaaagtaca catttctga atccttgtcc tccaatttag acgataagac tatgcacgag | 960 |
| ctatacgctt ggccctcgc tgacgctgtt agagctggtg ttggttccgt catgtgttcc | 1020 |
| tacaaccaaa ttaacaactc ttacggttgt caaaactcta agttgttgaa cggtatttg | 1080 |
| aaagacgaaa tgggtttcca aggcttcgtg atgtctgact gggccgctca acacactggt | 1140 |
| gctgcttccg ctgttgctgg tctagacatg tctatgccag gtgatactgc cttcgactct | 1200 |
| ggttactctt tctggggtgg taacctaacc ttagctgtca ttaacggtac cgttccggcc | 1260 |
| tggagagtcg atgacatggc tttgagaatc atgtctgctt tcttcaaggt tggtaagact | 1320 |
| atcgaagact tgccagacat taacttctct cctggactc gtgacacctt cggtttcgtt | 1380 |
| cacactttcg cccaagaaaa cagggaacaa gtcaacttcg gtgtaaatgt tcaacacgac | 1440 |
| cataagtccc acatcagaga agctgctgct aagggtccg tcgttttgaa gaacaccggt | 1500 |
| tccttgccat tgaagaaccc aaagttttg gctgtaatcg gtgaggacgc tggtccaaac | 1560 |
| ccagctggtc caaatggttg cggtgataga ggttgtgata acggtactct agctatggct | 1620 |
| tgggggttccg gcacttctca attcccttac ctaattaccc cagatcaagg tttatctaac | 1680 |
| agagctactc aagacggtac tagatacgaa tctatttga ctaataacga gtgggcttct | 1740 |

```
gtccaagccc tagtttccca accaaacgtc accgctatcg ttttcgctaa cgccgactct    1800
ggtgaaggtt acattgaagt tgacggcaac tttggtgaca gaaagaactt gactttgtgg    1860
caacaaggtg acgaactaat caagaacgtt tcttctatct gtccaaacac catcgtcgtt    1920
ttgcataccg ttggtccagt tctattggct gactacgaaa agaacccaaa cattaccgct    1980
atcgtttggg ctggtctacc aggtcaagaa tctggtaacg ccatcgccga tttgctatac    2040
ggtaaggttt ccccaggtcg ttctccattc acctggggta gaaccagaga atcctacggt    2100
accgaagttt tgtacgaagc caacaacggt agaggtgctc cgcaagatga cttcagtgaa    2160
ggtgttttca tcgactacag acacttcgat aagtacaaca ttactcccat ctacgaattc    2220
ggtcacggtt tatcctggtc caccttcaag ttcagtaact tgcacatcca aaagaacaat    2280
gtcggtccta tgtctccacc taacggcaag accatcgctg ctccatcttt gggaaacttc    2340
tccaaaaact tgaaggacta cggtttccca agaacgtcc gtcgtattaa ggaattcatt    2400
tacccatact taaacaccac tacctccggt aaggaagcct ctggtgatgc tcactacgga    2460
caaactgcta agaattctt gccagctggt gccttggatg ttctccaca accaagatct    2520 gccgcttctg gtgaaccagg tggtaacaga caattatacg atatcttgta caccgtcact    2580
gccaccatca ccaacactgg ttccgtcatg gatgatgctg tcccacaatt atacttgtca    2640
cacggtggtc caaacgaacc accaaaggtc ttgagaggtt tcgacagaat cgaaagaatt    2700
gccccaggtc aatctgttac attcaaggct gacttgacta gaagagactt atctaactgg    2760
gacaccaaga agcaacaatg ggtcattacc gattacccaa aaaccgtcta cgttggttct    2820
tcttccagag atttgccatt gtcagctaga ttgccataa                            2859
```

<210> SEQ ID NO 16
<211> LENGTH: 2661
<212> TYPE: DNA
<213> ORGANISM: Artificial Sequence
<220> FEATURE:
<223> OTHER INFORMATION: synthetic DNA

<400> SEQUENCE: 16

```
atgctactcc aagcattcct ttttctgtta gcaggatttg ctgccaaaat ctctgctgct      60
gtcgctttgg cctctgccgt tccagacact ctagccggtg tcaagaaggc tgacgcccaa    120
aaggtcgtga ctagagacac tttggcttac agcccaccac actacccatc tccttggatg    180
gacccaaacg ctgtcggttg ggaagaagcc tacgctaagg ccaagtcctt cgtctctcaa    240
ttgaccttga tggaaaaggt caatttaacc accggtgttg gttggcaagg tgaaagatgt    300
gtcggtaacg ttggatccat ccctagattg ggtatgcgtg gtttgtgttt gcaagacggt    360
ccattgggta tcagattgtc tgactacaac tcagctttcc ctgctggtac taccgccggt    420
gcttcttggt ctaagtcctt gtggtacgaa agaggtttgt tgatgggtac cgaatttaag    480
gaaaagggta ttgatatcgc tttggtcct gccacaggtc ctttgggtag aactgctgct    540
ggtggtagaa actgggaagg tttcaccgtc gacccataca tggctggcca cgctatggcc    600
gaagccgtta agggtatcca agacgctggt gttatcgctt gtgctaagca ctacattgcc    660
aacgaacaag aacactttag acaatctggt gaagtccaat ccagaaagta caacatttct    720
gaatccttgt cctccaattt agacgataag actatgcacg agctatacgc ttggccctc    780 gctgacgctg ttagagctgg tgttggttcc gtcatgtgtt cctacaacca aattaacaac    840
tcttacggtt gtcaaaactc taagttgttg aacggtattt tgaaagacga atgggttc    900
```

| | |
|---|---|
| caaggcttcg tgatgtctga ctgggccgct caacacactg gtgctgcttc cgctgttgct | 960 |
| ggtctagaca tgtctatgcc aggtgatact gccttcgact ctggttactc tttctggggt | 1020 |
| ggtaacctaa ccttagctgt cattaacggt accgttccgg cctggagagt cgatgacatg | 1080 |
| gctttgagaa tcatgtctgc tttcttcaag gttggtaaga ctatcgaaga cttgccagac | 1140 |
| attaacttct cttcctggac tcgtgacacc ttcggtttcg ttcacacttt cgcccaagaa | 1200 |
| aacagggaac aagtcaactt cggtgtaaat gttcaacacg accataagtc ccacatcaga | 1260 |
| gaagctgctg ctaagggttc cgtcgttttg aagaacaccg gttccttgcc attgaagaac | 1320 |
| ccaaagtttt tggctgtaat cggtgaggac gctggtccaa cccagctgg tccaaatggt | 1380 |
| tgcggtgata gaggttgtga taacggtact ctagctatgg cttggggttc cggcacttct | 1440 |
| caattccctt acctaattac cccagatcaa ggtttatcta acagagctac tcaagacggt | 1500 |
| actagatacg aatctatttt gactaataac gagtgggctt ctgtccaagc cctagtttcc | 1560 |
| caaccaaacg tcaccgctat cgttttcgct aacgccgact ctggtgaagg ttacattgaa | 1620 |
| gttgacggca actttggtga cagaaagaac ttgactttgt ggcaacaagg tgacgaacta | 1680 |
| atcaagaacg tttcttctat ctgtccaaac accatcgtcg ttttgcatac cgttggtcca | 1740 |
| gttctattgg ctgactacga aaagaaccca acattaccg ctatcgtttg ggctggtcta | 1800 |
| ccaggtcaag aatctggtaa cgccatcgcc gatttgctat acggtaaggt tccccaggt | 1860 |
| cgttctccat tcacctgggg tagaaccaga gaatcctacg gtaccgaagt tttgtacgaa | 1920 |
| gccaacaacg gtagaggtgc tccgcaagat gacttcagtg aaggtgtttt catcgactac | 1980 |
| agacacttcg ataagtacaa cattactccc atctacgaat tcggtcacgg tttatcctgg | 2040 |
| tccaccttca gttcagtaa cttgcacatc caaaagaaca atgtcggtcc tatgtctcca | 2100 |
| cctaacggca agaccatcgc tgctccatct ttgggaaact tctccaaaaa cttgaaggac | 2160 |
| tacggtttcc caaagaacgt ccgtcgtatt aaggaattca tttacccata cttaaacacc | 2220 |
| actacctccg gtaaggaagc ctctggtgat gctcactacg gacaaactgc taaagaattc | 2280 |
| ttgccagctg gtgccttgga tggttctcca caaccaagat ctgccgcttc tggtgaacca | 2340 |
| ggtggtaaca gacaattata cgatatcttg tacaccgtca ctgccaccat caccaacact | 2400 |
| ggttccgtca tggatgatgc tgtcccacaa ttatacttgt cacacggtgg tccaaacgaa | 2460 |
| ccaccaaagg tcttgagagg tttcgacaga atcgaaagaa ttgccccagg tcaatctgtt | 2520 |
| acattcaagg ctgacttgac tagaagagac ttatctaact gggacaccaa gaagcaacaa | 2580 |
| tgggtcatta ccgattaccc aaaaaccgtc tacgttggtt cttcttccag agatttgcca | 2640 |
| ttgtcagcta gattgccata a | 2661 |

<210> SEQ ID NO 17
<211> LENGTH: 2622
<212> TYPE: DNA
<213> ORGANISM: Artificial Sequence
<220> FEATURE:
<223> OTHER INFORMATION: synthetic DNA

<400> SEQUENCE: 17

| | |
|---|---|
| atgagattct ctggtatcgt cgctacccta gtcgctggtg ccggtgtctc tgctcaccca | 60 |
| ggtgattact ctaagttgga aagaagagct gtcgctacct ccgaaccaca ctacccacaa | 120 |
| ccatggatga acccagatgc cgacggttgg caagaagctt acgtcaaggc taaggacttc | 180 |
| gtttctcaaa tgaccttgtt ggaaaaggtc aacttaacta ctggtgtcgg ttgggcttcc | 240 |
| gatttgtgtg tcggtaacgt cggtgctgtt ccacgtttgg gtttgagatc cctgtgctta | 300 |

```
caagactctc caactggtgt cagattcgct gactgggttt ccgtgttccc agctggtatc    360
accaccggtg ccaccttcga caagggtcta atgtaccgta gaggtcaagc tatgggtcaa    420
gaagctaagg acaagggtat aaacgttttg ttgggtccag tcgccggtgg tttgggcaga    480
gttgctgctg gtggtagagc ttgggaatcc ttcggtgctg acccagtctt aactggttac    540
ggtatgattg aaactattaa gggtattcaa gacactggcg ttatcgctac tgctaagcac    600
ttcatcggta acgaacaaga acacttcaga caagttggtg aagaacgtgg tagaggtgtc    660
aacatctctg aatccttgtc ctctaacatt gatgataaga ctatgcatga actatacttg    720
tggccattcg ccgacgctgt tagagccggt gtcggctctg ttatgtgttc ctacactcaa    780
gttaacaact cctacggttg tcaaaactct aagttgttga acggtctatt gaaggatgaa    840
ttaggcttcc aaggtttcgt tatgtccgac tggcaagctc aacacaccgg tgccgcctct    900
gctgctgctg gtttggacat gtctatgcct ggtgacactg aattcaacac cggtctatcc    960
ttctggggtg ccaacttgac tttggctgtt gttaacggca ccgttgccga atggagaatc   1020
gatgacatgg ctatgagaat catggctgct ttcttcaaag tcggtaacac cctagaccaa   1080
ccagaaatca acttctcctc ctggaccaag gatactttcg gtccattgca ctcttctagt   1140
ggtaacagaa tccaacaaat taaccaacac gttgacgtca aagagatca cggtaaccta   1200
atcagagaag ttgctgctaa gggtactgtc ttgttgaaga acaccaacaa cgctttgcca   1260
ttgaataagc caaagttctt ggctgtcatt ggtgatgatg ctggttctaa ccccagaggt   1320
cctaacggtt gtccagatag aggatgtttg ttgggtacct gggtatggc ttggggttct   1380
ggcactgctg acttcccata cttaattacc ccagacgctg ccttgcaagc caagccatc   1440
gaagacggta cccgttacga atctatcttg tctaattacg ccaccgccca aactcaagct   1500
ttggtctctc aaacatacgc cactgctatt gttttcgtcg ctgcctcttc cggcgaaggt   1560
tacatcgatt tgacggcaa caagggtgac agaaacaatt tgactttgtg gtacgacggt   1620
gactcttggg ttaagaacgt ttcttctgtc tgtaacaaca ccatcgttgt tatccactct   1680
actggtccta ccatcttgac cgaatggtac gacaaccta atgtcaccgc tatcgtctgg   1740
gctggtgttc caggtcaaga atctggtaga gccatcactg acgttttgta cggtagagtt   1800
aacccagctg gtcgttctcc attcacctgg ggtaagacta gagaatccta cggtactgat   1860
gttatgtaca agccaaacaa cggtaacgaa gctccacaac aagactacac cgaaggtgtt   1920
ttcattgact acagacactt tgaccaacaa aaggatgaac cagtctacga atttggtcac   1980
ggtttgtcct acacaacctt cgaatacagt aacatcaggg ttgataaggc tccagcctct   2040
gaatacaaac caactactgg tcaaaccatc ccagctcctg ttttcggtgc taacgtttct   2100
aaggatttga tcaatacac tttcccatcc gacgaattc cacacatcta cttgtttatc   2160
tacccgtact tgaacaccct ctcttctggt gaagaagctt ccagagaccc aaagtacggt   2220
ggtaccgctg aggaattctt gccacctaag gccttagacg ttccccaca accattgcca   2280
agagcttctg gtaagaactc tccaggtggt aacagacaat tgtacgacac cttatacact   2340
gttactgcca ccattaccaa taccggtaag ttggttggtg aagaagttcc acaactatac   2400
gtttcccacg tggtccaga agacccacca gttgtgttgc gtggtttcga agaattaga   2460
ttagacccag tcaatccgc tactttcaag gttgatttga ccagaagaga cgtctctaac   2520
tgggacgtca aggtccaaga ctgggtcatc tccgagcatc aaagaaggt cttcgttggt   2580
tcctcctcta gaaagttgca cttgtctgct gacttgaact aa               2622
```

<210> SEQ ID NO 18
<211> LENGTH: 2823
<212> TYPE: DNA
<213> ORGANISM: Artificial Sequence
<220> FEATURE:
<223> OTHER INFORMATION: synthetic DNA

<400> SEQUENCE: 18

| | | | | | |
|---|---|---|---|---|---|
| atgagattcc | catctatttt | caccgctgtc | ttgttcgctg | cctcttctgc | cttggctgct | 60 |
| ccagtcaata | ccaccactga | agacgaaacc | gctcaaattc | cagccgaagc | tgttattggt | 120 |
| tacttggact | tggaaggtga | cttcgatgtc | gctgttttgc | cattctccaa | ctccaccaac | 180 |
| aacggcttgc | tattcatcaa | caccactatc | gcttctattg | ctgctaagga | agaaggtgtt | 240 |
| tccttggaca | agcgtcatcc | tggtgattac | tccaagttgg | aaagaagagc | tgtcgctacc | 300 |
| tccgaacctc | actaccccca | accatggatg | aacccagacg | ctgacggttg | gcaagaagct | 360 |
| tacgtgaagg | ccaaggattt | cgtctcccaa | atgaccctat | agaaaaggt | aacttaact | 420 |
| accggtgttg | gttgggcctc | tgatctatgt | gtcggtaacg | tcggtgctgt | tccaagatta | 480 |
| ggcttgagat | ctttgtgttt | acaagattct | ccaaccggtg | tccgtttcgc | tgactgggtt | 540 |
| tctgtcttcc | cagctggcat | caccactggt | gctaccttcg | acaagggttt | aatgtacaga | 600 |
| agaggccaag | ctatgggtca | agaagccaag | gacaaaggta | tcaacgtctt | gttgggtcca | 660 |
| gtcgccggtg | gtttgggtag | agttgctgct | ggtggtagag | cctgggagtc | tttcggtgcc | 720 |
| gatccagtct | tgacaggtta | cggtatgatt | gaaacaatta | agggtatcca | agacactggt | 780 |
| gttatcgcta | ccgctaaaca | cttcattggt | aacgaacaag | aacactttag | acaagttggt | 840 |
| gaagaaagag | gtagaggtgt | taacatctcc | gaatccttgt | cctctaacat | tgatgacaag | 900 |
| actatgcacg | aattgtactt | atggccattc | gctgacgctg | ttcgtgccgg | tgtcggttcc | 960 |
| gttatgtgtt | cctacacccca | agttaacaac | tcttacggtt | gtcaaaactc | taagttattg | 1020 |
| aacggtttat | tgaaggacga | attgggtttc | caaggtttcg | ttatgtccga | ctggcaagct | 1080 |
| caacacaccg | gtgctgcttc | tgctgccgcc | ggtttggata | tgtccatgcc | aggtgacacc | 1140 |
| gaattcaaca | ctggactatc | tttctgggt | gctaacttga | ccttggctgt | cgtcaacggt | 1200 |
| actgtcgctg | aatggagaat | agacgacatg | gccatgagaa | tcatggctgc | tttctttaag | 1260 |
| gtcggtaaca | ctttggatca | acccgaaatc | aacttctctt | cttggactaa | ggacactttc | 1320 |
| ggtccattgc | actcttcttc | tggtaacaga | atccaacaaa | taaaccaaca | cgtggacgtt | 1380 |
| agaagagacc | acgtaacctt | aatcagagaa | gttgccgcca | aaggcacagt | tttgctaaag | 1440 |
| aacactaaca | acgctttgcc | attgaacaag | ccaaagtttt | tggctgtcat | aggtgatgat | 1500 |
| gctggtagca | acccacgtgg | tccaaatggt | tgcccagaca | gaggttgttt | attgggtacc | 1560 |
| ttgggtatgg | cctggggttc | tggtaccgct | gacttcccat | acttaatcac | tccagacgcc | 1620 |
| gctttgcaag | ctcaagccat | cgaagatggt | actaggtacg | aatccatcct | gtccaactac | 1680 |
| gctactgctc | aaacccaagc | tttggttct | caaacctacg | ctaccgccat | cgtcttcgtc | 1740 |
| gctgcttcta | gtggtgaagg | ttacatcgat | ttcgacggta | acaagggtga | tagaaataac | 1800 |
| ttaactttgt | ggtacgacgg | tgactctttg | gtcaagaatg | tttcctccgt | ttgtaacaac | 1860 |
| accatcgtcg | taattcactc | taccggccct | actattttga | ccgagtggta | cgacaaccca | 1920 |
| aacgtaaccg | ctatcgtctg | gccggtgtt | ccgggtcaag | aatctggtag | agctatcact | 1980 |
| gacgttctat | acggtagagt | taaccctgct | ggtagatctc | cattcacttg | gggtaagacc | 2040 |
| agagaatctt | acggtactga | cgtcatgtac | aagccaaaca | acggtaacga | agctccacaa | 2100 |

```
caagactaca ctgaaggtgt cttcatcgac tacagacact tcgaccaaca aaaggatgaa    2160
cctgtttacg aattcggtca cggtttgtct tacaccacct tcgaatactc caacattaga    2220
gttgacaagg ccccagcctc tgaatacaag ccaactaccg gtcaaaccat cccagctcct    2280
gtttttggtg ccaacgtttc aaaggatttg agccaataca ctttcccatc tgatgaattc    2340
cctcacatct acttgttcat ttacccatac ctaaatactt cctcctccgg tgaagaagct    2400
tctagagatc aaagtacgg tggcaccgct gaagaattcc taccaccaaa ggctttggac    2460
ggttcaccac aaccattgcc aagagcctcc ggtaagaact ctcccggtgg caatcgtcaa    2520
ttgtacgaca ccttgtacac tgttactgct accatcacta acactggtaa gttggtcggc    2580
gaggaagtcc cacaattgta cgtctctcac ggtggccctg aagacccacc agtcgtcttg    2640
agaggtttcg aaagaattag actagatcca ggtcaatctg ccaccttcaa ggtcgaccta    2700
acccgtagag atgtttctaa ctgggacgtt aaggtccaag actgggttat ctccgaacac    2760
ccaaagaaag ttttgttgg ttcttcttcc cgtaagttgc atttgtctgc cgacctaaac    2820
taa                                                                  2823
```

<210> SEQ ID NO 19
<211> LENGTH: 1623
<212> TYPE: DNA
<213> ORGANISM: Artificial Sequence
<220> FEATURE:
<223> OTHER INFORMATION: synthetic DNA

<400> SEQUENCE: 19

```
atgagataca gaactgccgc tgccttggcc ttggccaccg gtccattcgc tagagctgat      60
agccactcca cttccggtgc ttcagctgaa gctgttgtcc caccagctgg tactccatgg     120
ggtactgctt acgataaagc caaggctgct ttggccaagc taaacttgca agacaaggtc     180
ggtattgtct ccggtgttgg ttggaacggc ggtccatgtg ttggaaacac atccccagct     240
tccaagattt cttacccttc tctatgtttg caagacggtc cattgggtgt cagatactct     300
actggttcca ctgctttcac cccaggtgtt caagccgcct ctacttggga cgttaacttg     360
atcagagaaa gaggtcaatt tatcggagaa gaagtcaagg cttctggtat ccacgttatt     420
ttaggtccag ttgctggtcc attgggtaag acccctcaag gtggtagaaa ctgggaaggt     480
ttcggcgtcg acccatactt gaccggtatc gccatgggtc aaaccatcaa cggtattcaa     540
tccgttggtg ttcaagccac tgccaagcac tacatcttga tgaacaaga attgaaccgt     600 gaaactatct cctccaaccc tgacgataga actttgcacg aattgtacac ctggccattc     660
gctgatgccg tccaagctaa cgtcgcttcc gtaatgtgta gttacaacaa ggttaacacc     720
acttgggctt gcgaagatca atacacatta caaaccgtct tgaaggacca attgggtttc     780
ccaggttacg tcatgactga ctggaacgcc caacacacca ccgttcaaag tgccaattct     840
ggtttggaca tgtctatgcc aggtaccgac ttcaacggta caacagact atggggtcca     900 gctttgacta acgctgttaa ctctaaccaa gttccaacct ccagagtcga cgacatggtt     960
actagaatct tggccgcttg gtacttgacc ggtcaagatc aagccggtta cccatctttc    1020
aacatttcta gaaacgtcca aggtaaccac aagactaacg ttagagccat cgctagagac    1080
ggtatcgtct tgttgaagaa cgacgctaac atcttaccat tgaaaaagcc agcttccatc    1140
gctgttgtcg gttctgctgc tatcattggt aatcacgcta gaaactcccc atcctgtaac    1200
gacaagggtt gtgacgatgg tgccttaggt atgggttggg gttccggtgc tgtcaattac    1260
```

```
ccatacttcg ttgctccata cgatgctatc aataccagag cttcctctca aggtacacaa    1320
gttaccttgt ctaacaccga taacacctct tccggtgctt ctgccgctcg tggtaaggat    1380
gtcgctattg tcttcattac tgctgactct ggtgaaggtt acatcaccgt cgaaggtaac    1440
gctggtgacc gtaacaactt ggaccettgg cacaatggta acgctttggt tcaagccgtt    1500
gctggtgcta actctaacgt tatcgttgtc gttcattctg tgggtgctat tatcttagaa    1560
caaatcttgg ccctaccaca agttaaggct gtcgtctggg ctggtttgcc atcccaagaa    1620
taa                                                                  1623
```

<210> SEQ ID NO 20
<211> LENGTH: 1821
<212> TYPE: DNA
<213> ORGANISM: Artificial Sequence
<220> FEATURE:
<223> OTHER INFORMATION: synthetic DNA

<400> SEQUENCE: 20

```
atgagattcc catctatctt cactgccgtc ttgttcgctg ccagttccgc tttggctgcc     60
ccagttaaca ccactaccga agatgaaacc gctcaaatcc ctgctgaagc tgtcatcggt    120
tacttagact tggaaggtga cttcgacgtg gccgtcttgc cttctctaa ctctaccaac    180 aacggtttgc tattcattaa cactaccatt gcttctatcg ccgccaagga agaaggtgtt    240
tctttggaca gagagactc tcactccacc tctggtgctt ccgccgaagc tgttgttccc    300
ccagctggta ctccatgggg taccgcttac gacaaggcta aggctgcttt ggccaagttg    360
aacttgcaag acaaggttgg tatcgtttcc ggtgtcggtt ggaacggtgg tccatgtgtc    420
ggtaatacct caccagcttc taagatctcc taccettcat tgtgtttgca agacggccct    480
ttgggtgtca gatactcaac tggctctacc gccttcactc aggtgttca agctgcttcc    540 acttgggatg ttaacttgat cagagagaga ggtcaattca tcggtgaaga agtcaaggct    600
tctggtattc atgtcatcct aggtccagtt gccggtccat gggcaagac cccacaaggt    660 ggtagaaact gggagggttt cggtgtggac ccatacttga ctggtatcgc tatgggtcaa    720
accatcaacg gtatccaatc tgtcggtgtt caagctaccg ctaagcacta cattttgaac    780
gaacaagaat taaacagaga aacaatttct tctaatccag acgacagaac cttacacgaa    840
ctatacacct ggccatttgc cgacgctgtg caagccaacg ttgcctctgt tatgtgctct    900
tacaacaagg ttaacaccac ttgggcttgt gaagaccaat acactttgca aactgtttta    960
aaagatcaat tgggtttccc aggttacgtg atgactgatt ggaacgctca acacactacc   1020
gtccaatccg ctaactctgg tttggacatg tccatgccag gtactgattt caacggtaac   1080
aaccgtttgt ggggtccagc tttgactaac gctgtcaact ccaaccaagt cccaacctcc   1140
agagttgacg acatggttac acgtatcttg gctgcttggt acctaactgg tcaagaccaa   1200
gctggttacc catcttttcaa catcagtaga aacgttcaag gtaaccacaa gaccaacgtc   1260
agagctattg ctagagatgg tatcgtcttg ttaaagaacg atgctaatat cttgccattg   1320
aagaagcccg cttctattgc tgttgttggt tccgctgcca tcattggtaa ccacgctaga   1380
aactctccat cttgtaacga caagggttgt gatgacggtg ctttgggtat gggttggggt   1440
agcggtgctg tcaactaccc atactttgtc gctccatacg acgctatcaa caccagagct   1500
tcttctcaag gtacccaagt taccttgtcc aacactgaca cacttcctc tggcgcctct   1560 gccgctagag gtaaggacgt tgctatcgtc ttcatcaccg ccgattctgg tgaaggttac   1620
attaccgtcg aaggtaacgc cggtgataga aacaacttgg acccatggca aacgggtaac   1680
```

```
gccttggtcc aagctgttgc tggtgctaac tccaatgtca tcgttgtcgt tcactctgtc    1740
ggagctatta ttttggaaca aatcttagct ttgcctcaag ttaaagctgt tgtttgggct    1800
ggtttgccat cccaagaata a                                              1821
```